United States Patent
Calvin et al.

(10) Patent No.: US 9,572,614 B2
(45) Date of Patent: Feb. 21, 2017

(54) MECHANISM FOR FACILITATING USER-CONTROLLED MANAGEMENT OF WEBPAGE ELEMENTS FOR DYNAMIC CUSTOMIZATION OF INFORMATION

(71) Applicant: salesforce.com, inc., San Francisco, CA (US)

(72) Inventors: Philip Norman Calvin, San Francisco, CA (US); Sonali Agrawal, San Carlos, CA (US); Beril Guvendik Maples, Oakland, CA (US); Eric Dorgelo, Vancouver (CA); Shelby Hubick, Vancouver (CA)

(73) Assignee: salesforce.com, inc., San Francisco, CA (US)

( * ) Notice: Subject to any disclaimer, the term of this patent is extended or adjusted under 35 U.S.C. 154(b) by 376 days.

(21) Appl. No.: 13/665,500

(22) Filed: Oct. 31, 2012

(65) Prior Publication Data
US 2014/0122993 A1     May 1, 2014

Related U.S. Application Data

(60) Provisional application No. 61/619,785, filed on Apr. 3, 2012.

(51) Int. Cl.
| | | |
|---|---|---|
| G06F 3/048 | (2013.01) | |
| G06F 17/00 | (2006.01) | |
| A61B 17/88 | (2006.01) | |
| G06F 17/30 | (2006.01) | |
| A61F 2/28 | (2006.01) | |

(52) U.S. Cl.
CPC ............ *A61B 17/8833* (2013.01); *A61F 2/28* (2013.01); *G06F 17/30893* (2013.01); *A61F 2002/2835* (2013.01)

(58) Field of Classification Search
CPC ............... G06F 17/30905; G06F 17/30893; G06F 17/3089
USPC .................................. 715/200, 234
See application file for complete search history.

(56) References Cited

U.S. PATENT DOCUMENTS

| | | |
|---|---|---|
| 5,577,188 A | 11/1996 | Zhu |
| 5,608,872 A | 3/1997 | Schwartz et al. |
| 5,649,104 A | 7/1997 | Carleton et al. |
| 5,715,450 A | 2/1998 | Ambrose et al. |

(Continued)

OTHER PUBLICATIONS

NetworkSolutions "Adding Content to Your Site", Apr. 12, 2011, pp. 1-3 http://www.networksolutions.com/support/adding-a-pre-built-widget-to-your-site/.*

(Continued)

*Primary Examiner* — Scott Badermen
*Assistant Examiner* — Mario M Velez-Lopez
(74) *Attorney, Agent, or Firm* — Blakely, Sokoloff, Taylor & Zafman

(57) ABSTRACT

In accordance with embodiments, there are provided mechanisms and methods for facilitating user-controlled management of webpage elements for dynamic customization of relevant information. In one embodiment and by way of example, a method includes receiving, in real-time, a request for performing one or more tasks relating to dynamic customization of webpage elements relating to a webpage package. The request may be received at a first computing device over a network. The method may further include performing, in real-time, the one or more tasks.

12 Claims, 18 Drawing Sheets

(56) References Cited

U.S. PATENT DOCUMENTS

| | | | |
|---|---|---|---|
| 5,761,419 A | 6/1998 | Schwartz et al. |
| 5,819,038 A | 10/1998 | Carleton et al. |
| 5,821,937 A | 10/1998 | Tonelli et al. |
| 5,831,610 A | 11/1998 | Tonelli et al. |
| 5,873,096 A | 2/1999 | Lim et al. |
| 5,918,159 A | 6/1999 | Fomukong et al. |
| 5,963,953 A | 10/1999 | Cram et al. |
| 6,092,083 A | 7/2000 | Brodersen et al. |
| 6,169,534 B1 | 1/2001 | Raffel et al. |
| 6,178,425 B1 | 1/2001 | Brodersen et al. |
| 6,189,011 B1 | 2/2001 | Lim et al. |
| 6,216,135 B1 | 4/2001 | Brodersen et al. |
| 6,233,617 B1 | 5/2001 | Rothwein et al. |
| 6,266,669 B1 | 7/2001 | Brodersen et al. |
| 6,295,530 B1 | 9/2001 | Ritchie et al. |
| 6,324,568 B1 | 11/2001 | Diec |
| 6,324,693 B1 | 11/2001 | Brodersen et al. |
| 6,336,137 B1 | 1/2002 | Lee et al. |
| D454,139 S | 3/2002 | Feldcamp |
| 6,367,077 B1 | 4/2002 | Brodersen et al. |
| 6,393,605 B1 | 5/2002 | Loomans |
| 6,405,220 B1 | 6/2002 | Brodersen et al. |
| 6,434,550 B1 | 8/2002 | Warner et al. |
| 6,446,089 B1 | 9/2002 | Brodersen et al. |
| 6,535,909 B1 | 3/2003 | Rust |
| 6,549,908 B1 | 4/2003 | Loomans |
| 6,553,563 B2 | 4/2003 | Ambrose et al. |
| 6,560,461 B1 | 5/2003 | Fomukong et al. |
| 6,574,635 B2 | 6/2003 | Stauber et al. |
| 6,577,726 B1 | 6/2003 | Huang et al. |
| 6,601,087 B1 | 7/2003 | Zhu et al. |
| 6,604,117 B2 | 8/2003 | Lim et al. |
| 6,604,128 B2 | 8/2003 | Diec |
| 6,609,150 B2 | 8/2003 | Lee et al. |
| 6,621,834 B1 | 9/2003 | Scherpbier et al. |
| 6,654,032 B1 | 11/2003 | Zhu et al. |
| 6,665,648 B2 | 12/2003 | Brodersen et al. |
| 6,665,655 B1 | 12/2003 | Warner et al. |
| 6,684,438 B2 | 2/2004 | Brodersen et al. |
| 6,711,565 B1 | 3/2004 | Subramaniam et al. |
| 6,724,399 B1 | 4/2004 | Katchour et al. |
| 6,728,702 B1 | 4/2004 | Subramaniam et al. |
| 6,728,960 B1 | 4/2004 | Loomans |
| 6,732,095 B1 | 5/2004 | Warshavsky et al. |
| 6,732,100 B1 | 5/2004 | Brodersen et al. |
| 6,732,111 B2 | 5/2004 | Brodersen et al. |
| 6,754,681 B2 | 6/2004 | Brodersen et al. |
| 6,763,351 B1 | 7/2004 | Subramaniam et al. |
| 6,763,501 B1 | 7/2004 | Zhu et al. |
| 6,768,904 B2 | 7/2004 | Kim |
| 6,782,383 B2 | 8/2004 | Subramaniam et al. |
| 6,804,330 B1 | 10/2004 | Jones et al. |
| 6,826,565 B2 | 11/2004 | Ritchie et al. |
| 6,826,582 B1 | 11/2004 | Chatterjee et al. |
| 6,826,745 B2 | 11/2004 | Coker et al. |
| 6,829,655 B1 | 12/2004 | Huang et al. |
| 6,842,748 B1 | 1/2005 | Warner et al. |
| 6,850,895 B2 | 2/2005 | Brodersen et al. |
| 6,850,949 B2 | 2/2005 | Warner et al. |
| 7,340,411 B2 | 3/2008 | Cook |
| 7,620,655 B2 | 11/2009 | Larsson et al. |
| 8,347,228 B1* | 1/2013 | Kates ........ G06Q 10/107 345/9 |
| 2001/0044791 A1 | 11/2001 | Richter et al. |
| 2002/0022986 A1 | 2/2002 | Coker et al. |
| 2002/0029161 A1 | 3/2002 | Brodersen et al. |
| 2002/0029376 A1 | 3/2002 | Ambrose et al. |
| 2002/0035577 A1 | 3/2002 | Brodersen et al. |
| 2002/0042264 A1 | 4/2002 | Kim |
| 2002/0042843 A1 | 4/2002 | Diec |
| 2002/0072951 A1 | 6/2002 | Lee et al. |
| 2002/0073125 A1* | 6/2002 | Bier ............ G06F 17/24 715/255 |
| 2002/0082892 A1 | 6/2002 | Raffel et al. |
| 2002/0129352 A1 | 9/2002 | Brodersen et al. |
| 2002/0140731 A1* | 10/2002 | Subramaniam ...... G06F 3/0481 715/762 |
| 2002/0143997 A1 | 10/2002 | Huang et al. |
| 2002/0152102 A1 | 10/2002 | Brodersen et al. |
| 2002/0161734 A1* | 10/2002 | Stauber ............. G06F 9/465 |
| 2002/0162090 A1 | 10/2002 | Parnell et al. |
| 2002/0165742 A1 | 11/2002 | Robins |
| 2003/0004971 A1 | 1/2003 | Gong et al. |
| 2003/0018705 A1 | 1/2003 | Chen et al. |
| 2003/0018830 A1 | 1/2003 | Chen et al. |
| 2003/0066031 A1 | 4/2003 | Laane |
| 2003/0066032 A1 | 4/2003 | Ramachandran et al. |
| 2003/0069936 A1 | 4/2003 | Warner et al. |
| 2003/0070000 A1 | 4/2003 | Coker et al. |
| 2003/0070004 A1 | 4/2003 | Mukundan et al. |
| 2003/0070005 A1 | 4/2003 | Mukundan et al. |
| 2003/0074418 A1 | 4/2003 | Coker |
| 2003/0088545 A1 | 5/2003 | Subramaniam et al. |
| 2003/0120675 A1 | 6/2003 | Stauber et al. |
| 2003/0151633 A1 | 8/2003 | George et al. |
| 2003/0159136 A1 | 8/2003 | Huang et al. |
| 2003/0187921 A1 | 10/2003 | Diec |
| 2003/0189600 A1* | 10/2003 | Gune ............. G06Q 10/0631 715/810 |
| 2003/0191743 A1 | 10/2003 | Brodersen et al. |
| 2003/0204427 A1 | 10/2003 | Gune et al. |
| 2003/0204810 A1* | 10/2003 | Dam ............. G06F 17/3089 715/255 |
| 2003/0204811 A1* | 10/2003 | Dam ............. G06F 17/3089 715/255 |
| 2003/0206192 A1 | 11/2003 | Chen et al. |
| 2003/0225730 A1* | 12/2003 | Warner ............. H04M 3/493 |
| 2004/0001092 A1 | 1/2004 | Rothwein et al. |
| 2004/0010489 A1 | 1/2004 | Rio |
| 2004/0015981 A1 | 1/2004 | Coker et al. |
| 2004/0027388 A1 | 2/2004 | Berg et al. |
| 2004/0128001 A1 | 7/2004 | Levin et al. |
| 2004/0186860 A1 | 9/2004 | Lee et al. |
| 2004/0193510 A1 | 9/2004 | Catahan, Jr. et al. |
| 2004/0199489 A1 | 10/2004 | Barnes-Leon et al. |
| 2004/0199536 A1 | 10/2004 | Barnes Leon et al. |
| 2004/0199543 A1 | 10/2004 | Braud et al. |
| 2004/0215719 A1* | 10/2004 | Altshuler ........... G06F 17/3089 709/204 |
| 2004/0217985 A9* | 11/2004 | Ries ............. G06F 17/3089 715/740 |
| 2004/0249854 A1 | 12/2004 | Barnes-Leon et al. |
| 2004/0260534 A1 | 12/2004 | Pak et al. |
| 2004/0260659 A1 | 12/2004 | Chan et al. |
| 2004/0268299 A1 | 12/2004 | Lei et al. |
| 2005/0050555 A1 | 3/2005 | Exley et al. |
| 2005/0091098 A1 | 4/2005 | Brodersen et al. |
| 2005/0240869 A1* | 10/2005 | Leetaru ............ G06F 17/30861 715/234 |
| 2006/0136822 A1* | 6/2006 | Kelly ............. G06F 17/3089 715/234 |
| 2006/0168127 A1* | 7/2006 | Kelly ............. G06F 17/212 709/219 |
| 2007/0162845 A1* | 7/2007 | Cave ............. G06F 17/218 715/209 |
| 2008/0215426 A1* | 9/2008 | Guldimann ......... G06Q 30/02 705/14.61 |
| 2008/0244740 A1* | 10/2008 | Hicks ............. G06F 17/24 726/22 |
| 2009/0228838 A1* | 9/2009 | Ryan ............. G09G 5/14 715/853 |
| 2009/0249239 A1* | 10/2009 | Eilers ............. G06F 17/24 715/769 |
| 2010/0042473 A1* | 2/2010 | Arora ............. G06Q 10/10 705/7.29 |
| 2010/0083102 A1* | 4/2010 | Jimenez ............. G06F 17/3089 715/255 |
| 2010/0115430 A1* | 5/2010 | Skirpa ............. G06F 17/2247 715/760 |
| 2011/0289065 A1* | 11/2011 | Wells ............. G06F 17/30905 707/706 |

(56) References Cited

U.S. PATENT DOCUMENTS

| | | | | |
|---|---|---|---|---|
| 2012/0047120 A1* | 2/2012 | Connolly | .......... | G06F 17/30864 |
| | | | | 707/706 |
| 2012/0254714 A1* | 10/2012 | Peters | .................. | G06F 17/243 |
| | | | | 715/209 |
| 2012/0290959 A1* | 11/2012 | Quine | ...................... | G06F 8/34 |
| | | | | 715/765 |
| 2013/0311890 A1* | 11/2013 | Cui | ........................ | H04L 41/22 |
| | | | | 715/736 |
| 2014/0053060 A1* | 2/2014 | Walker | ................ | G06F 17/2247 |
| | | | | 715/234 |
| 2014/0304682 A1* | 10/2014 | Taylor | ................ | G06F 9/45529 |
| | | | | 717/113 |

OTHER PUBLICATIONS

NetworkSolutions "Expert designers working for you" as available May 5, 2012, pp. 1-2 http://www.networksolutions.com/design-develop/index.jsp.*

* cited by examiner

MECHANISM FOR FACILITATING USER-CONTROLLED MANAGEMENT OF WEBPAGE ELEMENTS FOR DYNAMIC CUSTOMIZATION OF INFORMATION

CLAIM OF PRIORITY

This application claims the benefit of U.S. Provisional Patent Application No. 61/619,785, entitled "Page Widget Packaging and Reusability" by Philip Normal Calvin, et al., filed Apr. 3, 2012, the entire contents of which are incorporated herein by reference and priority is claimed thereof.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

One or more implementations relate generally to data management and, more specifically, to a mechanism for facilitating user-controlled management of webpage elements for dynamic customization of information.

BACKGROUND

In the growing world of computing technology, developing websites and portal sites is well-known; however, such conventional techniques for performing such tasks require high programming skills that typically computer programmers and system administers possess and are above and beyond the skills of a typical end-user. Certain template-based solutions have been proposed to provide some control to the users; however, such control is extremely trivial and limited in nature, such as being limited to website color selection, etc.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches.

In conventional database systems, users access their data resources in one logical database. A user of such a conventional system typically retrieves data from and stores data on the system using the user's own systems. A user system might remotely access one of a plurality of server systems that might in turn access the database system. Data retrieval from the system might include the issuance of a query from the user system to the database system. The database system might process the request for information received in the query and send to the user system information relevant to the request. The secure and efficient retrieval of accurate information and subsequent delivery of this information to the user system has been and continues to be a goal of administrators of database systems. Unfortunately, conventional database approaches are associated with various limitations.

BRIEF DESCRIPTION OF THE DRAWINGS

In the following drawings like reference numbers are used to refer to like elements. Although the following figures depict various examples, one or more implementations are not limited to the examples depicted in the figures.

DETAILED DESCRIPTION

Methods and systems are provided for facilitating user-controlled management of webpage elements for dynamic customization of relevant information. In one embodiment and by way of example, a method includes receiving, in real-time, a request for performing one or more tasks relating to dynamic customization of webpage elements relating to a webpage package. The request may be received at a first computing device over a network. The method may further include performing, in real-time, the one or more tasks.

As used herein, a term multi-tenant database system refers to those systems in which various elements of hardware and software of the database system may be shared by one or more customers. For example, a given application server may simultaneously process requests for a great number of customers, and a given database table may store rows for a potentially much greater number of customers. As used herein, the term query plan refers to a set of steps used to access information in a database system.

Embodiments are described with reference to an embodiment in which techniques for facilitating management of data in an on-demand services environment are implemented in a system having an application server providing a front end for an on-demand database service capable of supporting multiple tenants, embodiments are not limited to multi-tenant databases nor deployment on application servers. Embodiments may be practiced using other database architectures, i.e., ORACLE®, DB2® by IBM and the like without departing from the scope of the embodiments claimed.

Next, mechanisms and methods for facilitating user-controlled management of webpage elements for dynamic customization of relevant information will be described with reference to example embodiments.

Figure 1:
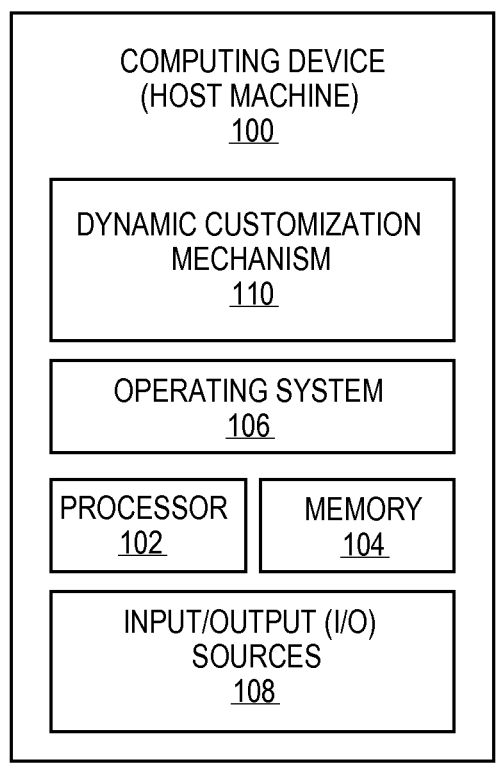
FIG. 1 illustrates a computing device employing a mechanism for facilitating user-controlled management of webpage elements for dynamic customization of relevant information according to one embodiment.

FIG. 1 illustrates a computing device 100 employing a mechanism for facilitating user-controlled management of webpage elements for dynamic customization of relevant information ("dynamic customization mechanism") 110 according to one embodiment. In one embodiment, computing device 100 serves as a host machine employing dynamic customization mechanism 110 for providing dynamic customization of information by facilitating user-based control of management of webpage elements (e.g., attributes, property, permission, widgets, etc.), as will be described further in this document.

Computing device 100 may include server computers (e.g., cloud server computers, etc.), desktop computers, cluster-based computers, set-top boxes (e.g., Internet-based cable television set-top boxes, etc.), and the like. Computing device 100 may also include smaller computers, such as mobile computing devices, such as cellular phones including smartphones (e.g., iPhone® by Apple®, BlackBerry® by Research in Motion®, etc.), handheld computing devices, personal digital assistants (PDAs), etc., tablet computers (e.g., iPad® by Apple®, Galaxy® by Samsung®, etc.), laptop computers (e.g., notebooks, netbooks, Ultrabook™, etc.), e-readers (e.g., Kindle® by Amazon.com®, Nook® by Barnes and Nobles®, etc.), Global Positioning System (GPS)-based navigation systems, etc.

Computing device 100 includes an operating system (OS) 106 serving as an interface between any hardware or physical resources of the computing device 100 and a user. Computing device 100 further includes one or more processors 102, memory devices 104, network devices, drivers, or the like, as well as input/output (I/O) sources 108, such as touchscreens, touch panels, touch pads, virtual or regular keyboards, virtual or regular mice, etc. It is to be noted that terms like "node", "computing node", "client", "client device", "server", "server device", "cloud computer", "cloud server", "cloud server computer", "machine", "host machine", "device", "computing device", "computer", "computing system", "multi-tenant on-demand data system", and the like, may be used interchangeably throughout this document. It is to be further noted that terms like "application", "software application", "program", "software program", "package", and "software package" may be used interchangeably throughout this document.

Figure 2:
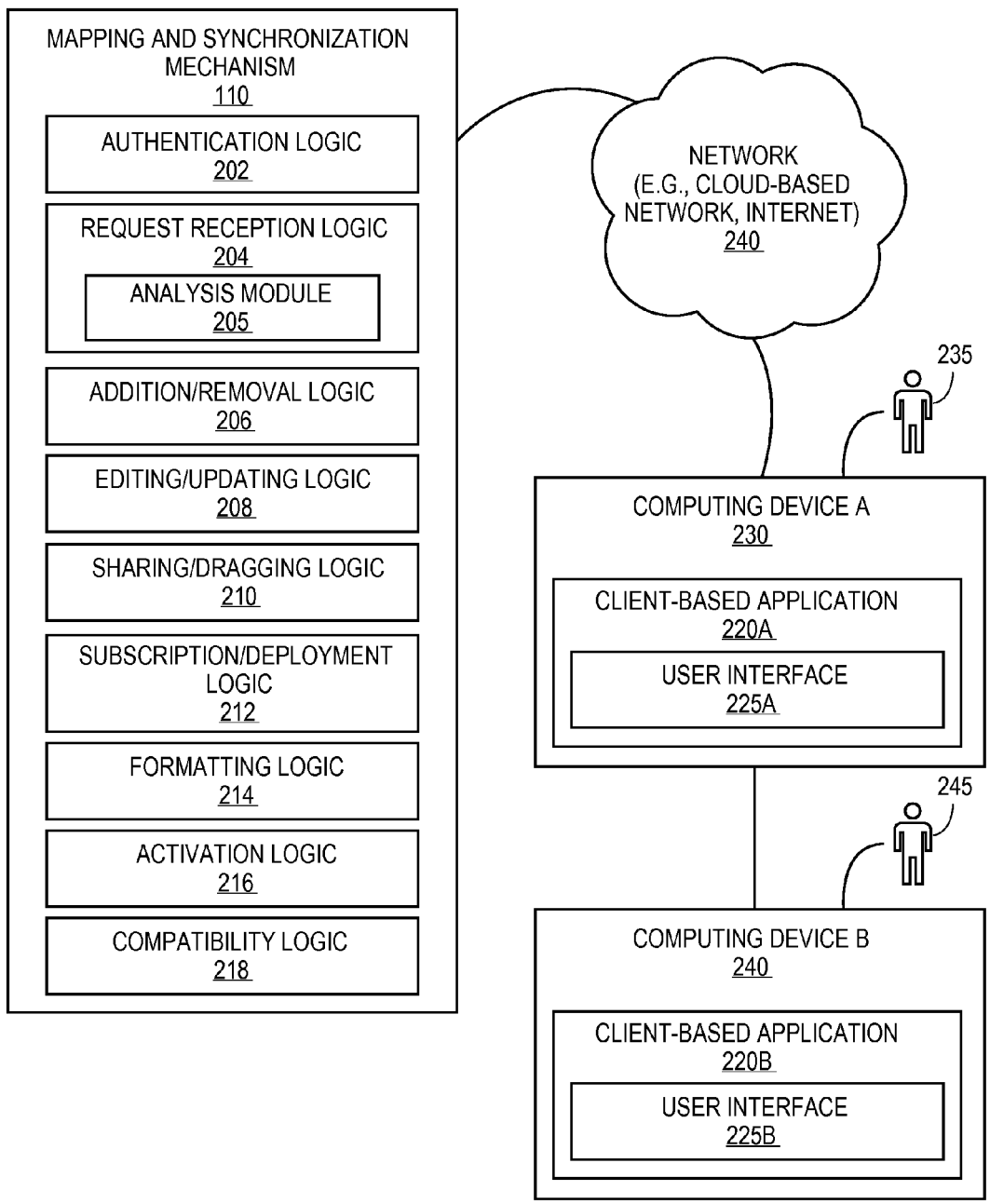
FIG. 2 illustrates a mechanism for facilitating user-controlled management of webpage elements for dynamic customization of relevant information according to one embodiment.

FIG. 2 illustrates a mechanism for facilitating user-controlled management of webpage elements for dynamic customization of information 110 according to one embodiment. In one embodiment, using dynamic customization mechanism 110, a user is allowed to manipulate (e.g., create, add, remove, define, deploy, share, etc.) webpage elements, such as widgets, to have dynamic and customized information for use. For example, having employed dynamic customization mechanism 110, various tools and techniques are provided to user 235, 245 to further modernize cross site sharing concepts of Salesforce.com®. Examples of users may include, but are not limited to, customers, such as organizational customers 235 (e.g., small and large businesses, companies, corporations, academic institutions, government agencies, non-profit organization, etc.) of the service provider (e.g., Salesforece.com) and/or individual customers 245, such as individuals or end-users, of the organization customers. It is to be noted that terms like "user", "customer", "organization", "business", "company", etc., may be used interchangeably throughout this document.

Examples of webpage elements include, but are not limited to, (1) an attribute (e.g., one of many properties, etc.), (2) a property (e.g., metadata descriptions of objects (e.g., page, body, etc.), lists (or collection) of attributes, etc.), (3) a permission (to describe what is or is not allowed, such as to, sometimes, check each action in the code base such that before one can perform an action (e.g., undo, redo, edit, delete, read, create, etc.), it is verified that permission to perform the action is granted, and (4) a widget (e.g., a component, an element, an extension, a container, a library item, etc.).

In one embodiment, dynamic customization mechanism 110 may be employed at a server computing system, such as computing device 100 of FIG. 1, and may be in communication with one or more client computing devices, such as client computing devices A 230 and B 240, over a network 250 (such as the Internet, a cloud computing network, etc.). As aforementioned, a user may include an organization or organizational customer 235, such as a company, a business, etc., that is a customer to a provider (e.g., Salesforce.com) that provides access to dynamic customization mechanism 110 (such as via client computer A 230). Similarly, a user may further include an individual or a small business 245, etc., that is a customer of the organization/organizational customer and accesses dynamic customization mechanism 110 via client computer B 240. Client computing devices 230, 240 may be the same as or similar to computing device 100 of FIG. 1 and include a mobile computing device (e.g., smartphones, tablet computers, etc.) or larger computers (e.g., desktop computers, server computers, etc.)

In one embodiment, dynamic customization mechanism 110 facilitates user-based control of website or webpage elements, such as allowing users/customers 235, 245 to, via their respective computing devices 230, 240, manipulate webpage elements, including from creating an element to maintaining it to deleting it, etc., to receive and have dynamic information. For example, customer/user A 235 may include a package delivery company (e.g., Federal Express, United Parcel Service (UPS), etc.) that is provided control over webpage elements to manipulate the business information in the matter it suits it and provides some or all of that information to its customers, such as customer/user B 240, in a particular format. The provider of dynamic customization mechanism 110 may extend the same user-control features to customer B 245, who is a customer of customer A 235, so that customer B 245 may also manipulate various webpage elements such that the customer A's website may be formatted and its information may be customized as desired or necessitated by customer B 245. As aforementioned, customer A 235 may access various customization features provided by dynamic customization mechanism 110 via user interface 225A and using client-based application 220A that may be downloaded on client computer A 230. Similarly, customer B 245 may access the customization features via user interface 225B and using client-based application 220B that may be downloaded on client computer B 240.

In the illustrated embodiment, dynamic customization mechanism 110 includes various components, such as authentication logic 202, request reception logic 204, addition/deletion logic 206, editing/updating logic 208, sharing/dragging logic 210, subscription/deployment logic 212, formatting logic 214, activation logic 216, and compatibility logic 216. Throughout this document, the term "logic" may be interchangeably referred to as "component" or "module" and may include, by way of example, software, hardware, and/or any combination of software and hardware, such as firmware. This combination of components 202-218 provides user-based control of webpage elements without having to require any computer or website or Internet programming qualifications or skills (in contrast to the conventional systems that require a user to be a skilled computer programmer).

In one embodiment, authentication logic 202 may be used to authenticate the user/customer 235, 245 and/or their respective computing devices 230, 240 before they are allowed to make changes to the webpage elements. It is contemplated that the authentication process may be a one-time process conducted when computing devices 230, 240 are first allowed access to dynamic customization mechanism 110 via their corresponding client applications 220A, 220B or, in some embodiments, authentication may be a recurring process that is performed each time a request for customization (placed via one or more client applications 220A, 220B and further via one or more user interfaces 225A, 225B) is received by request reception logic 204 at dynamic customization mechanism 110 at the cloud-based server computer over network 250.

For example, to increase functionality, a user/customer 235, 245 decides to build a new widget and places a corresponding request, via a client application 220A, 220B at a computing device 230, 240. The request may be received at request reception logic 204 (and, if necessary, authenticated by authentication logic 202) and forwarded on to addition/deletion logic 206 to process the request to add or create or build a new widget, as requested. For example, the process of building or creating a new widget may include selecting a page element (including page elements that are containers) and the new widget may be created from the selected page element. As a result, any dependent object, such as data queries or stylesheet rules, may be automatically included in the widget. Further, additional JavaScript and CSS may be provided (such as by users 235, 245 via computing devices 230, 240), as necessary, to make the new widget perform as desired or necessitated by user 235, 245. For example, in some embodiments, the potential set of JavaScript and CSS files may be defined as a list of external files that are on the page, while the actual selected list may be its subset. Further, for example, user 235, 245 may provide a name and a description for the new widget and additional options, such as "available for deployment" or "active" may also be selectable by user 235, 245. Once created, the new widget may appear in the widgets section on the overview design page. If the new widget being created is a blank widget, it may be given a name and a description and contain a single panel that serves as the root. Further, in some embodiments, the new widget may not be deployed until user 235, 245 selects to deploy it, which may then be deployed using deployment logic 214.

Now, if one or more of users 235, 245 wish to remove or delete a widget (whether it be a newly created or an existing widget), a request for removal of a widget is placed, via one or more client applications 220A, 220B, with request reception logic 204. As aforementioned, the request may be authenticated, if necessary, and forwarded on to addition/deletion logic 206 to initiate and perform the process of removal of the requested widget. To avoid any accidental removals of webpage elements, the removal process may request users 235, 245 to explicitly confirm (such as by clicking an "okay" or "confirm" or "yes" button) that the requested widget is to be removed. Upon confirmation, the widget may be deleted from the overview tab. It may also be removed from, for example, the left-hand side of the page and other sections, such as click-to-add sections of the page. In some embodiments, the removal of a widget may not disable its existing usage and that they continue to remain unchanged, while, in other embodiments, the removal of the widget may disable all existing usage. Further, the widget's usage may be displayed for users' benefit before the widget is removed and any existing usage of the widget may be continued to be tracked even after the removal.

A selective property editing of a widget may be performed or requested to be performed by user 235, 245 using editing/updating logic 206, where a property may include widget parameters, such as input parameters to filter, sorts of repeater in the widget, uniform resource locators (URLs), and other widget parameters, etc. The property may be a free form text box or it can be configured to be a picklist, such as a lookup from, for example, a content list. For example, user 235, 245, via client application 220A, 220B at computing device 230, 240, may select any property from the original hierarchy and make it available to the widget user, or when a parameterized widget is used on a webpage, the site designer may then be prompted for any parameter values that are inputted. The selection of the property from the original hierarchy may include embedding EL syntax into custom code and content blocks that are automatically picked up as parameters, and selectively picking CSS rules or properties that may be surfaced. Further, any possible parameters values for these selective properties may be from the same set of parameter types as, for example, Data Queries (e.g., specified, query string, etc.). This type of custom-property specification may be found in many stories (e.g., templates, widgets, queries, themes, forms, custom-properties, schemas, etc.) and may be found to be consistent across multiple platforms.

Similarly, user 235, 245 may edit an existing widget by opening an existing widget in a page editor and then, editing any available custom properties and the composition of the widget. Further, any existing deployed widgets may not be impacted by such editing. In one embodiment, editing facilitate by and performed through editing/updating logic 208 in response to editing request placed via client application 220A, 220B and received at request reception logic 204.

Using dynamic customization mechanism 110, via sharing/dragging logic 210, user 235, 245 may be facilitated further control to perform additional functions, such as dragging and/or sharing of a webpage element, etc. For example, a draggable widget may appear in the left side of the webpage along with other draggable components, such as an image, a content block, etc. Additionally, another property for a widget, when creating one, may be to create an icon corresponding to the widget. This way, a default icon for widgets may also allow user 235, 245 to choose to customize it per each widget that is created. For example, as facilitated by sharing/dragging logic 210, user 235, 245, via client application 220A, 220B and user interface 225A, 225B, may drag and drop or click to add a widget, where the widget is copied into a new page as a copy of a component, while the dependent parts and pieces may be copied into their appropriate location. An original widget may be considered a complete entity if its sub-items may not be selected. Like dragging, using sharing/dragging logic 210, a widget may be shared within a site network, such as widgets shared from a parent website may automatically be made available to its child websites. Further, once a child site is linked to a parent site via a site network, then a package may be made available for its use like any other resources that are part of that site network. In other words, a package may become any other resource that can be included in a site network.

In one embodiment, subscription/deployment logic 212 may facilitate subscription and/or deploying of webpage elements, such as subscribing a widget from a depot or a database. For example, user 235, 245 may request, via client application 220A, 220B, to select widgets from one or more available depots associated with a website accessible to user 235, 245. In some embodiments, a site that deploys a widget or package may not change anything in that package; while, in other embodiments, the widget or package can be edited after it is deployed and until it is redeployed anyone using it may have no visibility into the pending changes, such as a widget may be classified as read-only, except for its exposed properties that remain evident and obvious. In one embodiment, user 235, 245 may request to open a widget from an overview tab and edit it in a studio environment, where the studio environment may act identically to a page editor environment, except it may not contain an actual page object, so that no page is selectable. Further, the root page element may not be deleted and that editing a widget may not necessarily or automatically affect the activated version or any downstream versions that are already being used. If user 235, 245 wishes to update a widget to its latest state, in one embodiment, the update may be automatically deployed by subscription/deployment logic 212.

Similarly, as facilitated by subscription/deployment logic 212 and sharing/dragging logic 210, user 235, 245 may request deployment or redeployment of a widget or a package into a studio using a drag/drop feature as well as build and share their widgets within an organization via a site network within that organization and/or share across various organizations. Further, a deployed widget may appear on the LHS toolbar and may be clicked to be added to a toolbox. It is contemplated that an already deployed widget may be redeployed as necessitated or desired by user 235, 245.

In one embodiment, dynamic customization mechanism 110 further includes formatting logic 214 to facilitate various other formatting and/or editing features, such as user 235, 245 may want to push a widget version to various sites and components that are employed and being used. For example, a push update may be used to cause all existing usages to update their work in progress and published states to the newly-activated widget. Further, in some embodiments, a newly-activated widget may be automatically published; while, in other embodiments, the newly-activated widget may be used in work-in-progress and user 235, 245 may choose to request its deployment and may further choose to auto-publish it as part of the deployment. In one embodiment, with various aforementioned processes, a widget, whether it be newly created or updated or deployed or shared, etc., may be activated using activation logic 216 of dynamic customization mechanism 110. Compatibility logic 218 allows for dynamic customization mechanism 110 to work with any number and types of webpage elements, client computing devices 230, 240, networks 250, and the like.

It is contemplated that any number and type of components may be added to and/or removed from dynamic customization mechanism 110 to facilitate various embodiments including adding, removing, and/or enhancing certain features. For brevity, clarity, and ease of understanding of dynamic customization mechanism 110, many of the standard and/or known components, such as those of a computing device, are not shown or discussed here. It is contemplated that embodiments are not limited to any particular technology, topology, system, architecture, and/or standard and are dynamic enough to adopt and adapt to any future changes.

Figure 3:
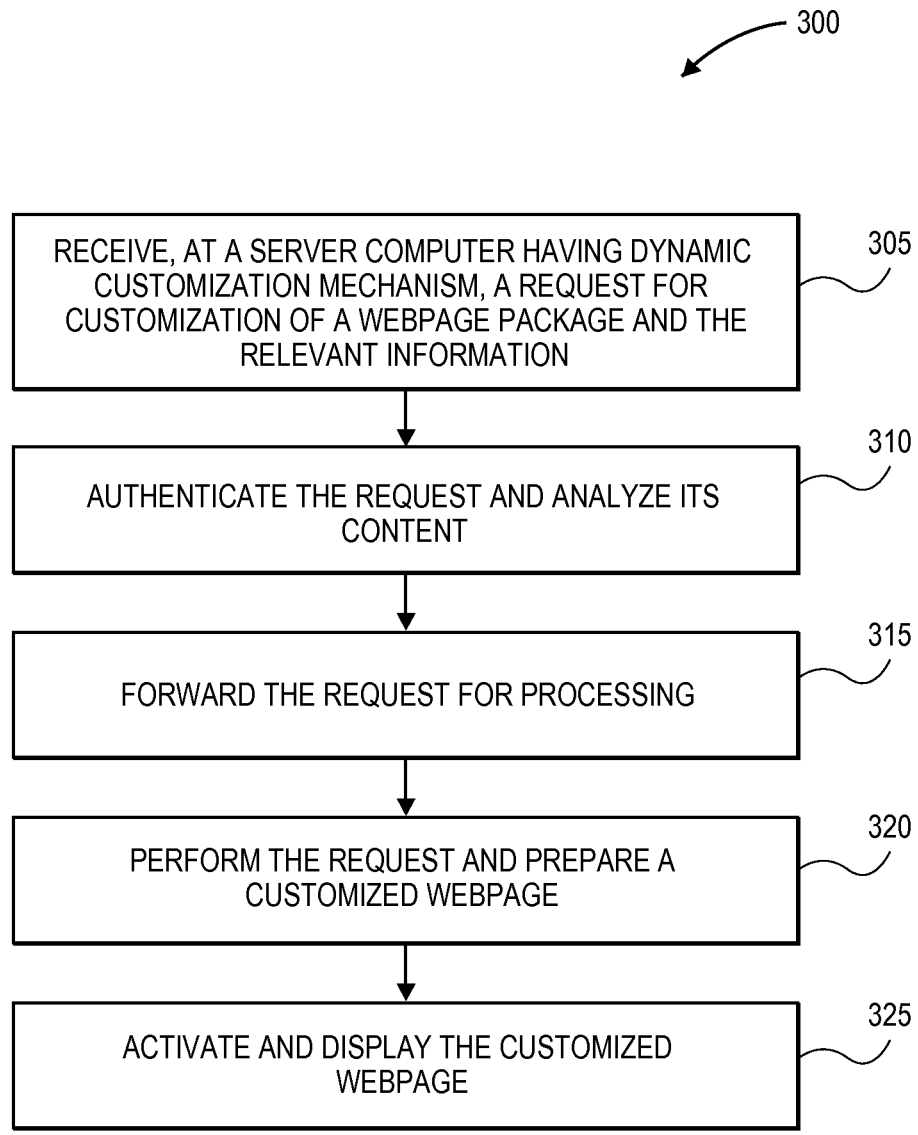
FIG. 3 illustrates a method for facilitating user-controlled management of webpage elements for dynamic customization of relevant information according to one embodiment.

FIG. 3 illustrates a method 300 for facilitating user-controlled management of webpage elements for dynamic customization of relevant information according to one embodiment. Method 300 may be performed by processing logic that may comprise hardware (e.g., circuitry, dedicated logic, programmable logic, etc.), software (such as instructions run on a processing device), or a combination thereof. In one embodiment, method 300 may be performed by dynamic customization mechanism 110 of FIG. 1.

Method 300 begins at block 305 with receiving, at a server computer having dynamic customization mechanism 110 of FIG. 1, a request for customization of a webpage package and the relevant information, where the request may have been placed by a user using a computing device (e.g., a server computer, a desktop computer, a mobile computing device, such as a smartphone, a tablet computer, etc.) having a client-based application, such as client applications 220A, 220B of FIG. 2. As has been previously discussed in the document, a webpage package may include webpage elements, such as attributes, properties, permissions, widgets, etc. Further, as aforementioned, a customization request may include a request for any number of changes, such as adding, updating, deleting, sharing, subscribing, deploying, etc., of a webpage element so that the user may have customized information.

Upon reception of the request, at block 310, the request is authenticated which may include analyzing any relevant information. As aforementioned, in some embodiments, the authentication process may be performed merely once and may not be repeated (e.g., authentication the user/customer and/or the computing device being used by the user); whereas, in other embodiments, the authentication process may be performed repeatedly for each request. At block 315, upon authentication of the request, the request is forwarded on to one or more components of dynamic customization mechanism 110 as illustrated in FIG. 2 for performance of the request. At block 320, the request is performed and a customized webpage is prepared. At block 325, the customized webpage having customized information is displayed to the user via a display device of (or in communication with) the client computing device.

Figure 4A:
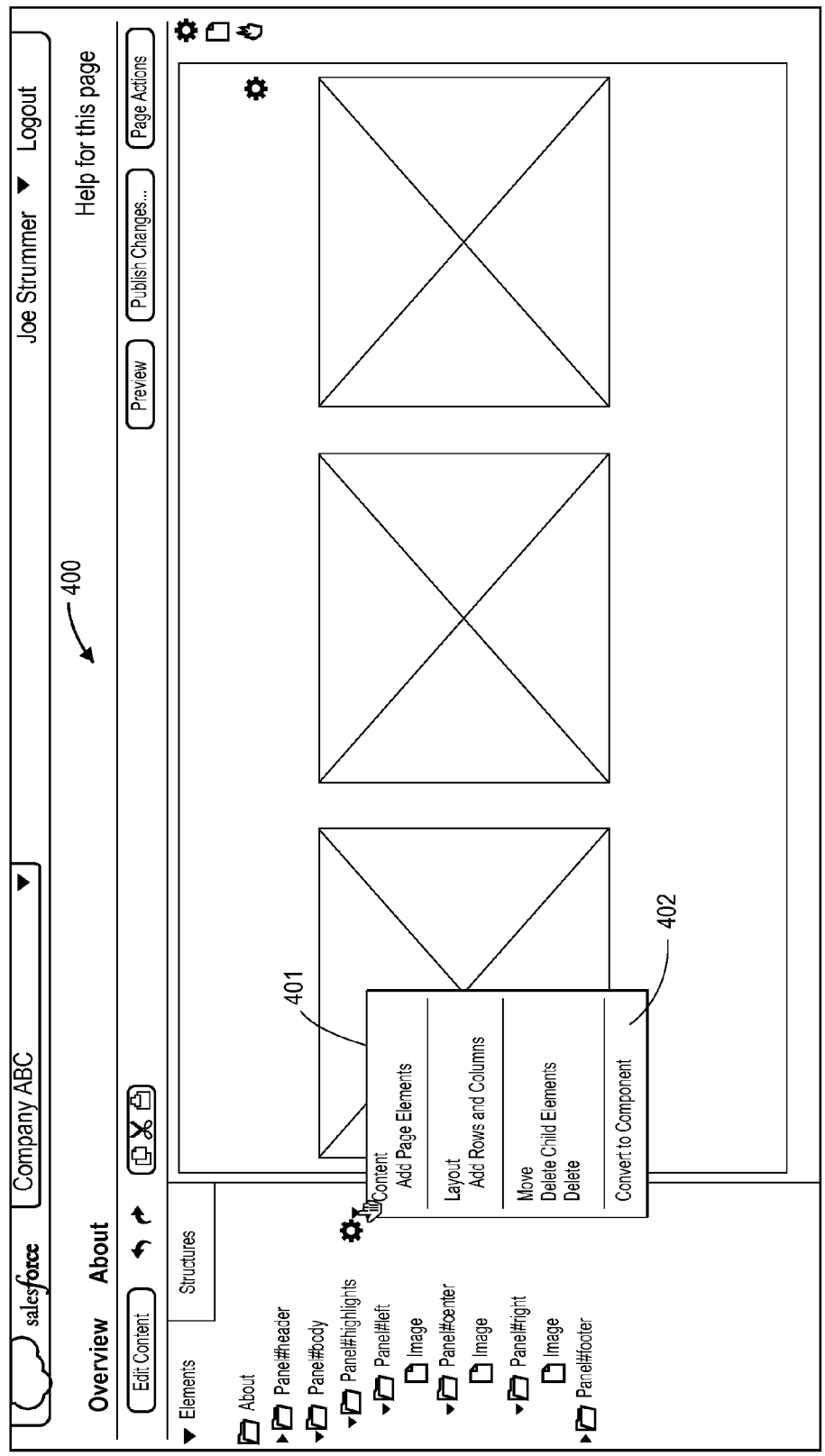
FIGS. 4A-4L illustrate screenshots representing of the aforementioned processes of facilitating user-controlled manipulation of webpage elements and dynamic customization of relevant information according to one embodiment.
Figure 4B:
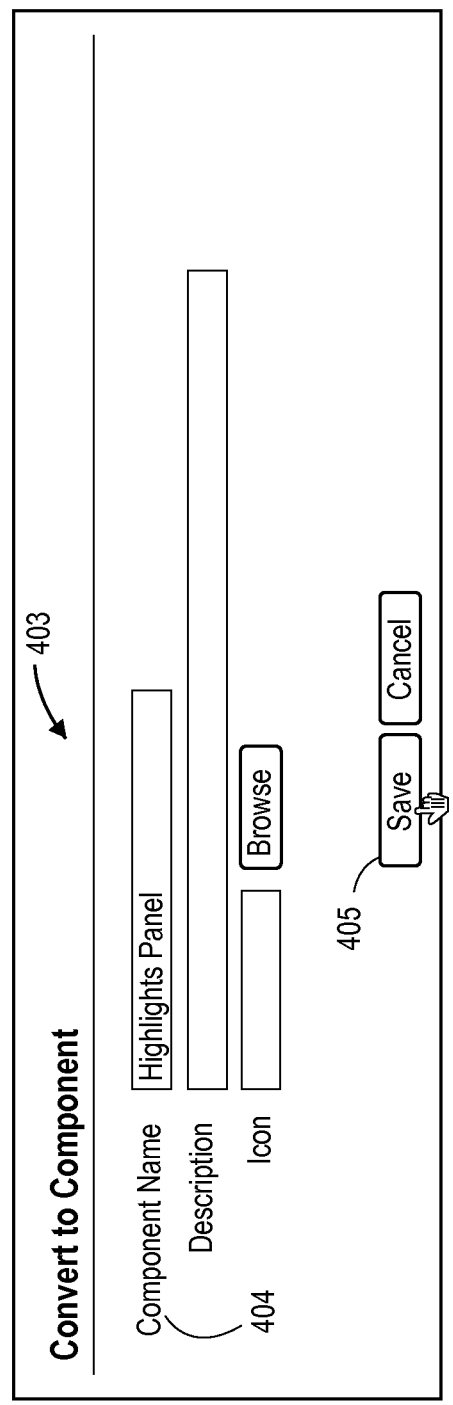

FIGS. 4A-4L illustrate screenshots representing of the aforementioned processes of facilitating user-controlled manipulation of webpage elements and dynamic customization of relevant information according to one embodiment. FIG. 4A illustrates a screenshot 400 representing a left-hand side action menu 401 which is shown to include a number of options, such as adding, deleting, converting, etc. In the illustrated embodiment, convert to component 402 option is chosen which results in a convert to component overlay page 403, in FIG. 4B, requiring the user to input some basic information, such as component name 404, description, icon, etc. Once the necessary information is entered, such as the component name 404 (e.g., highlights panel, as illustrated), a save button 405 may be clicked to open the new component, e.g., highlights panel, as new tab 406 in FIG. 4C.

Figure 4C:
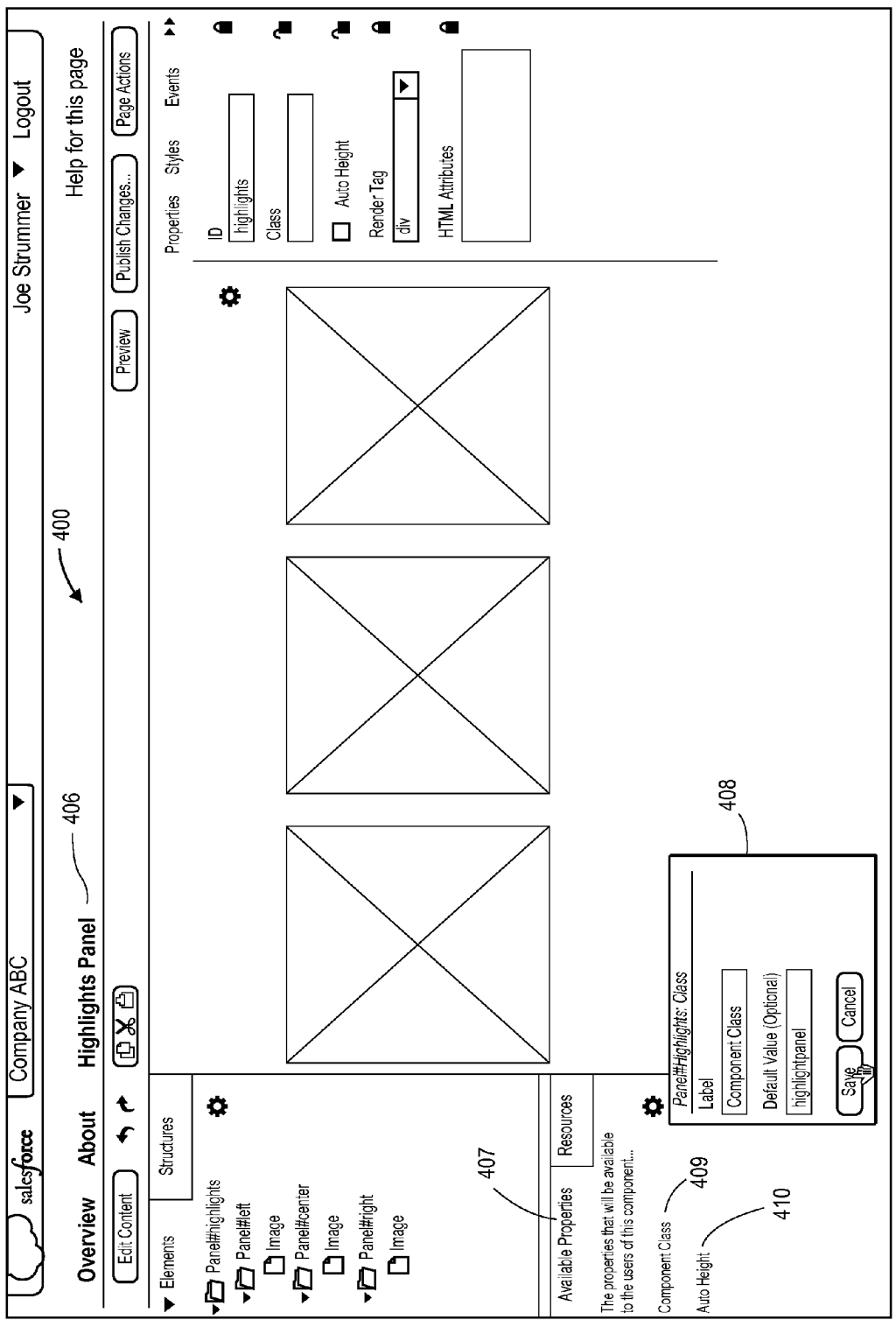

Screenshot 400, as illustrated in FIG. 4C, further shows a list of available properties 407 (such as component class, auto height, etc.) on the left side of the page 400. Any one of the available properties 407 may be clicked to open component creator 408 so that the user may choose to alter any relevant information, such as component label, default value (if any), etc., as desired or necessitated. Similarly, using component creator 408, any number and type of new properties may be added to the list of the properties 407 as well as reordering of the existing properties may be performed by a simple act of dragging, such as the illustrated auto height 410 may be moved up, while component class 409 may be moved down. For example, screenshot 400 of FIG. 4D illustrates an additional property, center image alt text 411, along with auto height 410 being listed to the top and component class 409 listed as second.

Figure 4D:
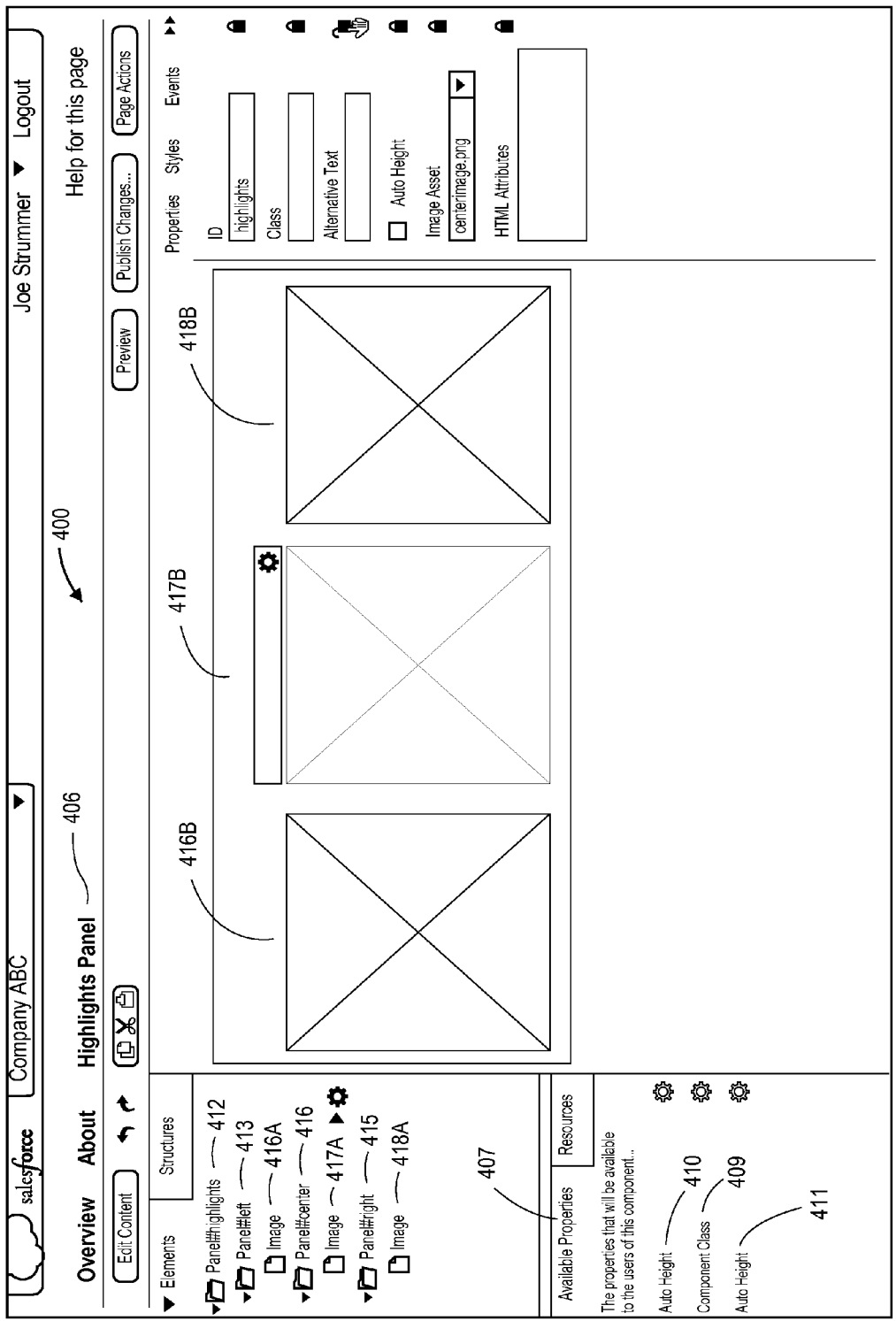
Figure 4E:
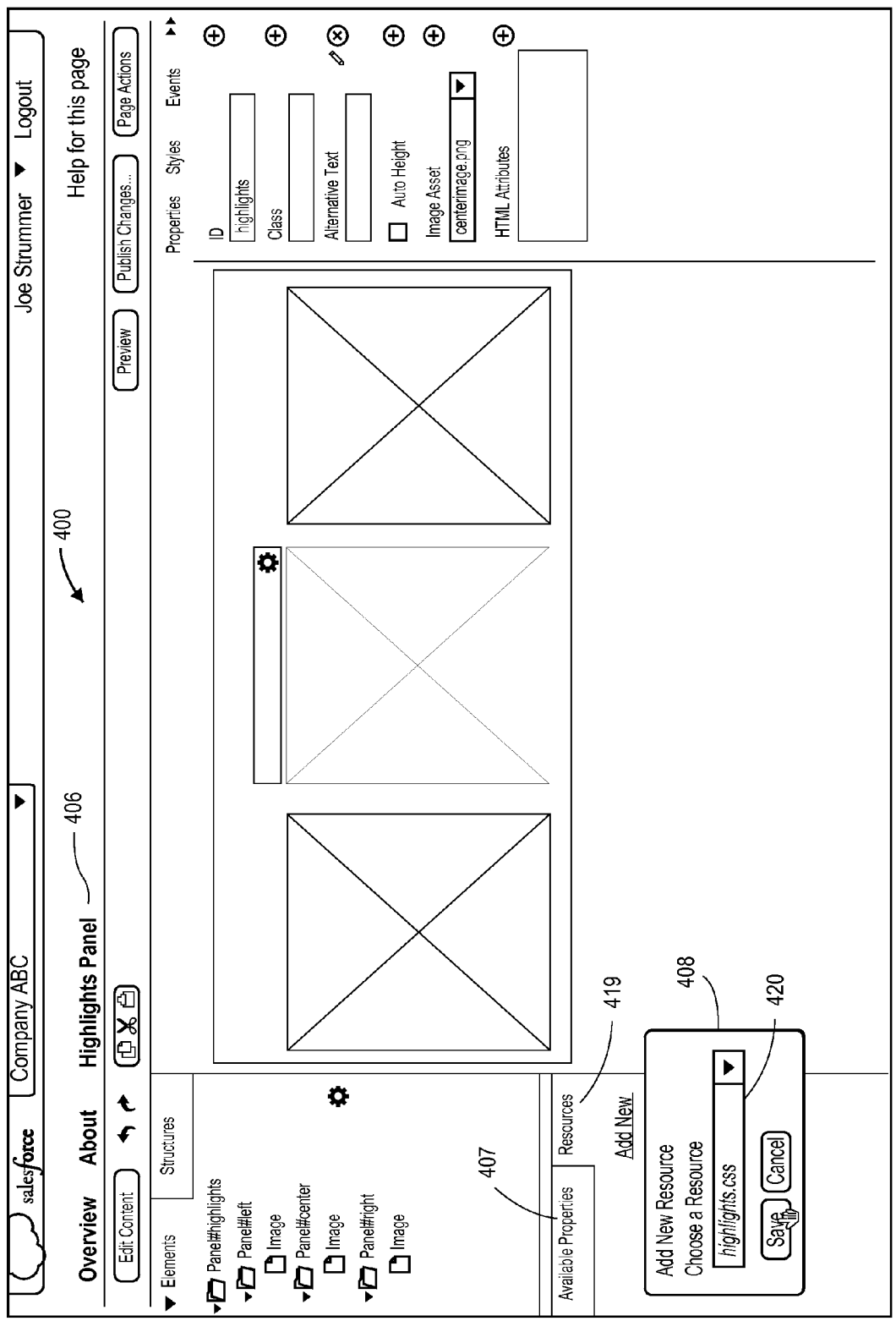
Figure 4F:
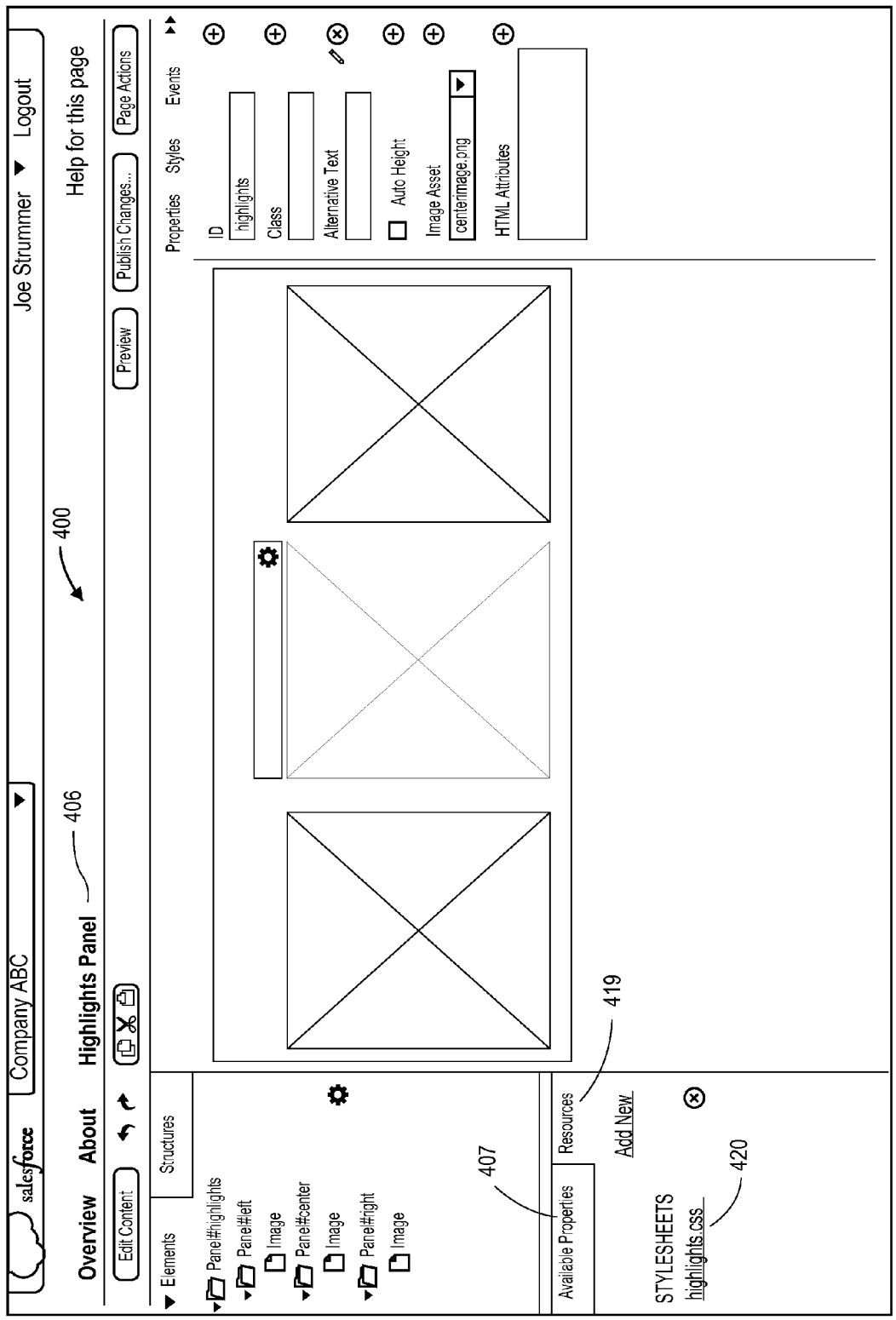

In one embodiment, the left side of page 400, in FIG. 4D, further illustrates panel highlights 412 including panels left 413, center 414 and right 415. The panels 413, 414, 415 list images 416A, 417A, 418A corresponding to images 416B, 417B, 418B, respectively. For example and as illustrated, when image 417A is selected for editing, its corresponding image 417B is highlighted. FIG. 4E illustrates that component creator 408 of FIG. 4C may also be used to create/add, delete/remove and edit available resources 419 and not only properties 407 as shown in FIG. 4C. In FIG. 4E, component creator 408 is shown as being used to add a new resource, hightlights.css 420, while FIG. 4F show hightlights.css 420 as being added under resources 419. In one embodiment, component creator 408 may be used by users to manually add, delete or edit any resources, such css, javascript, etc.

Figure 4G:
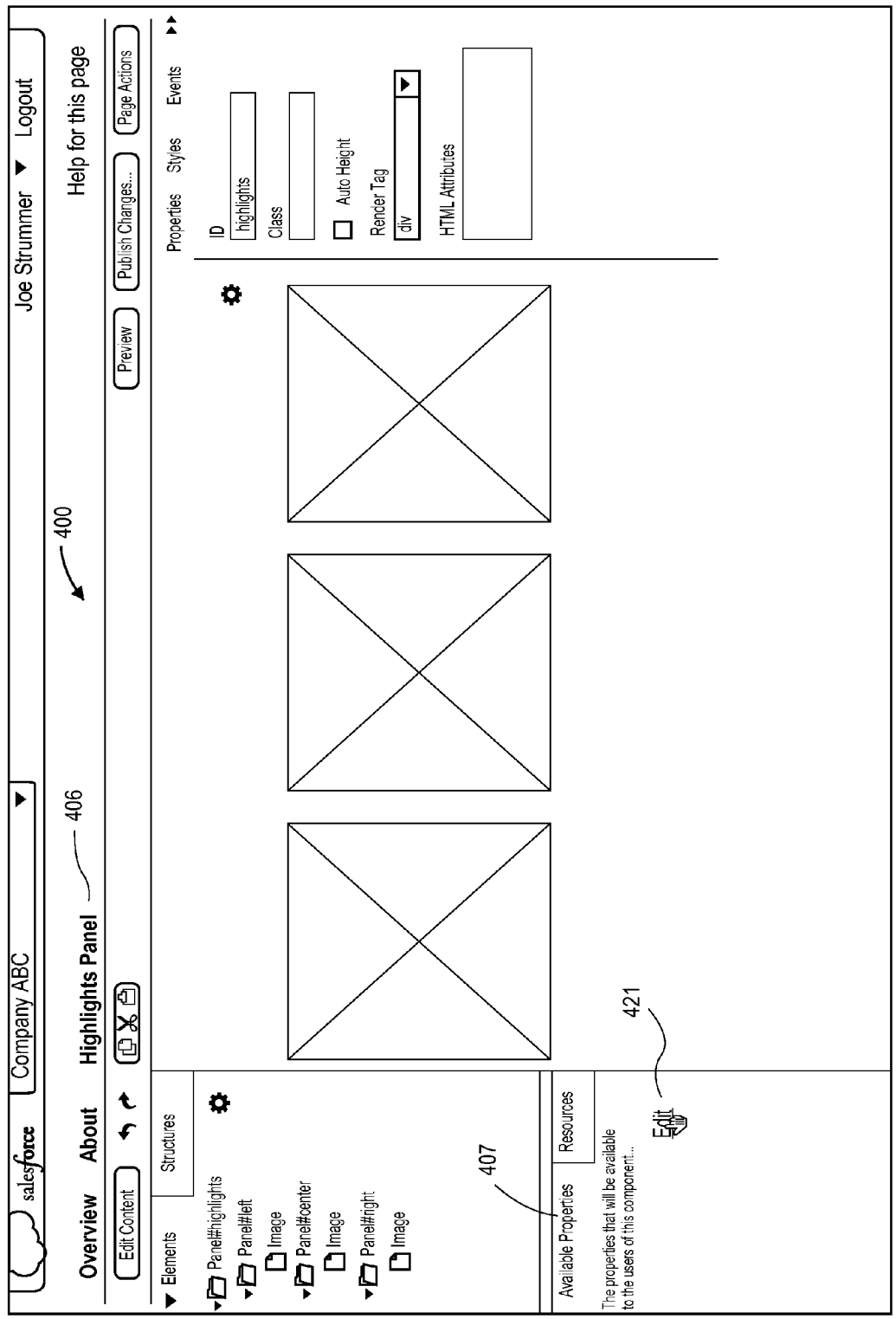
Figure 4H:
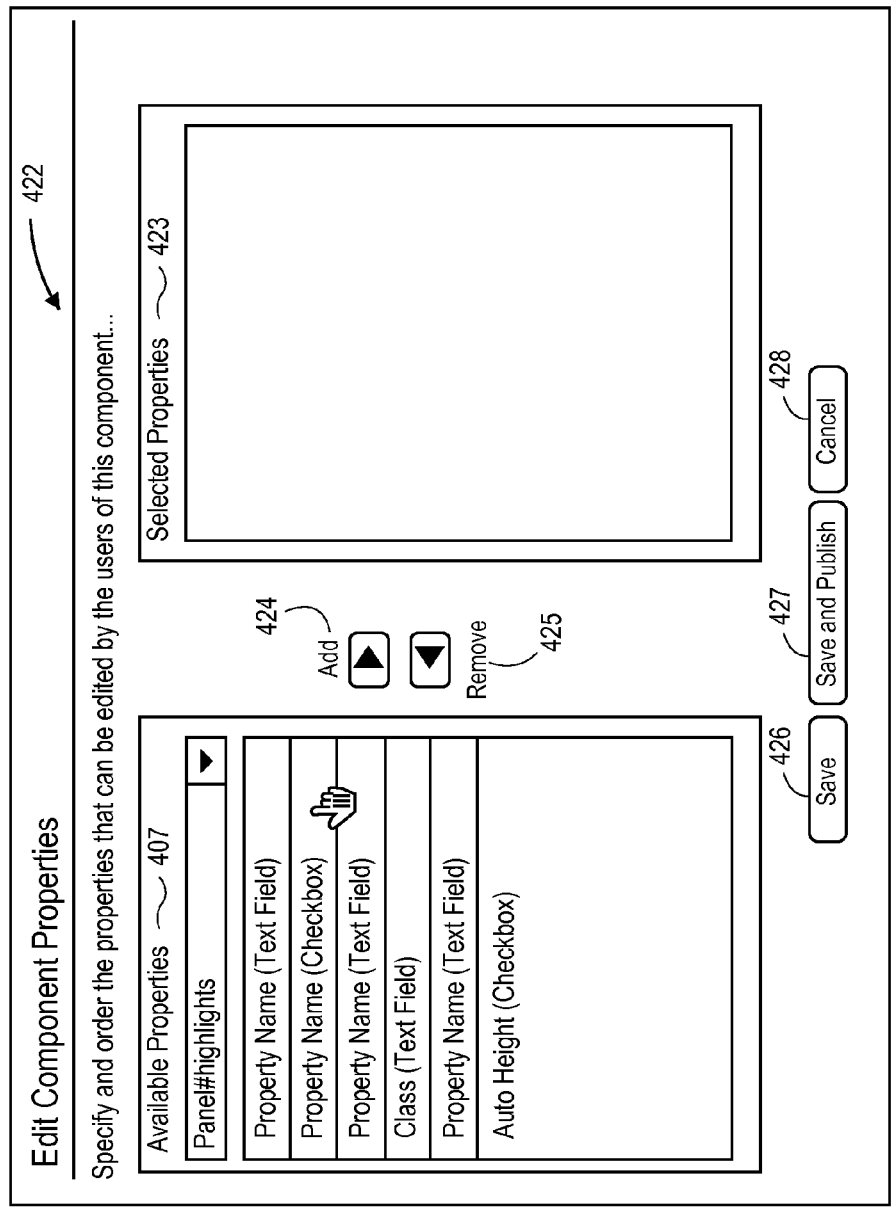
Figure 4I:
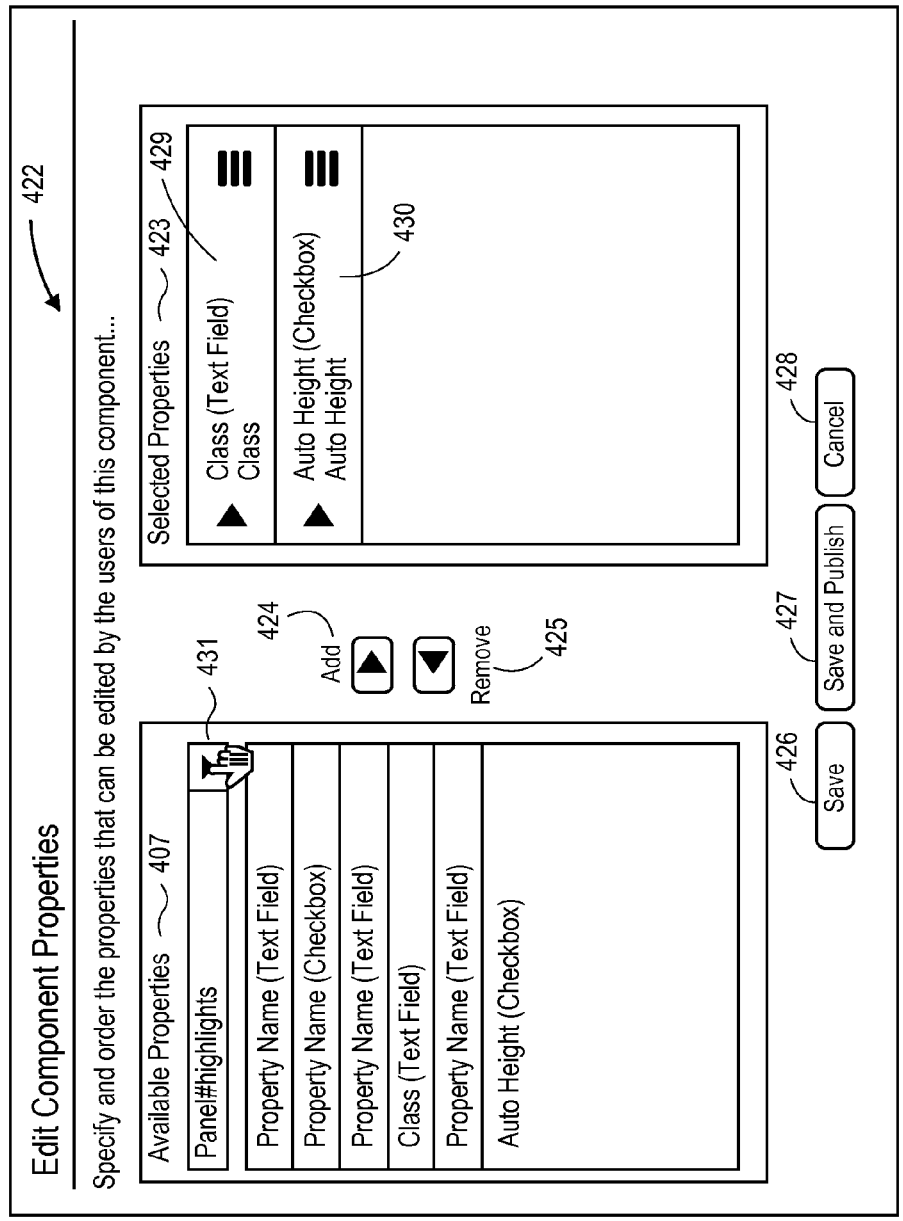
Figure 4J:
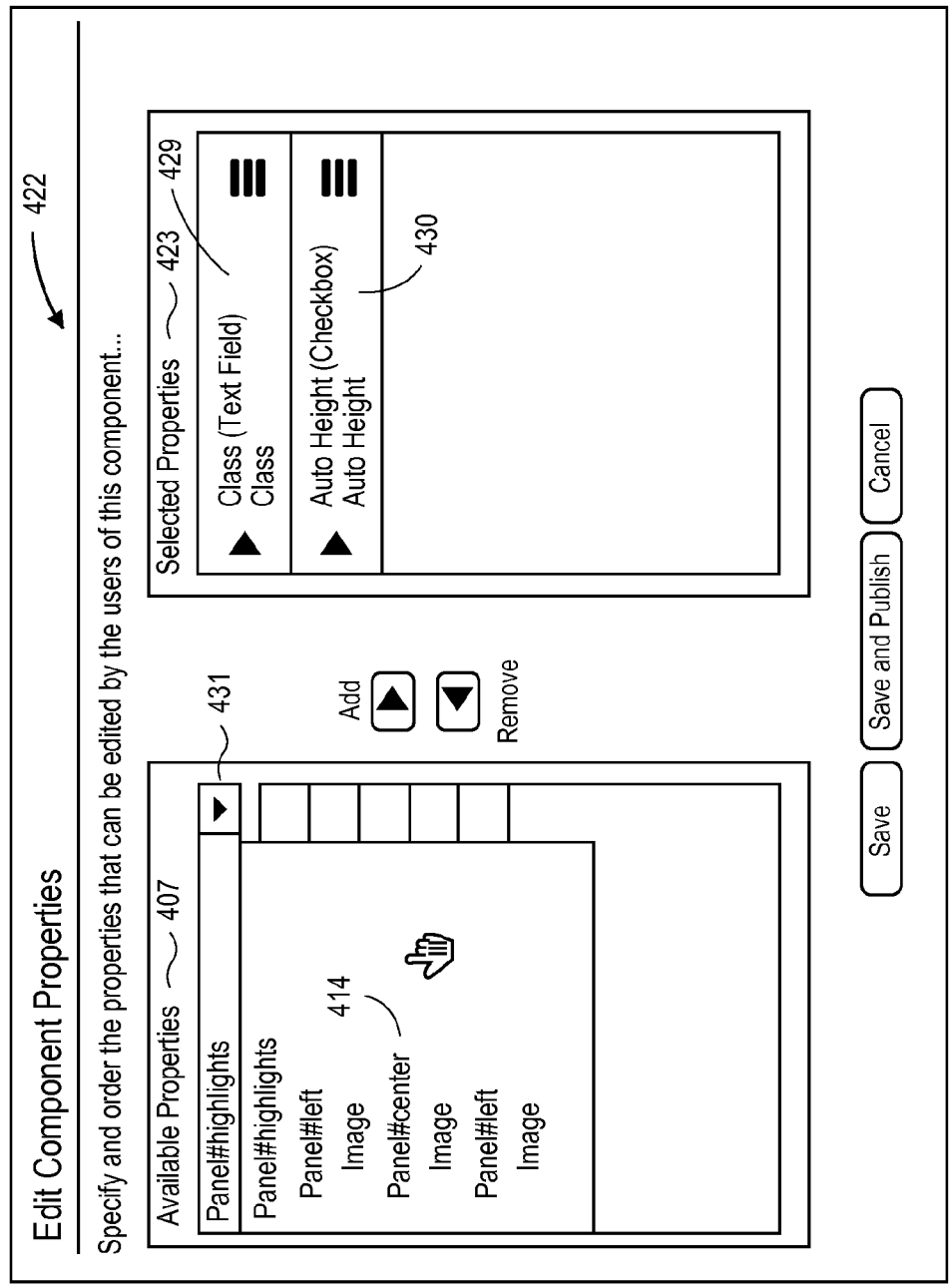
Figure 4K:
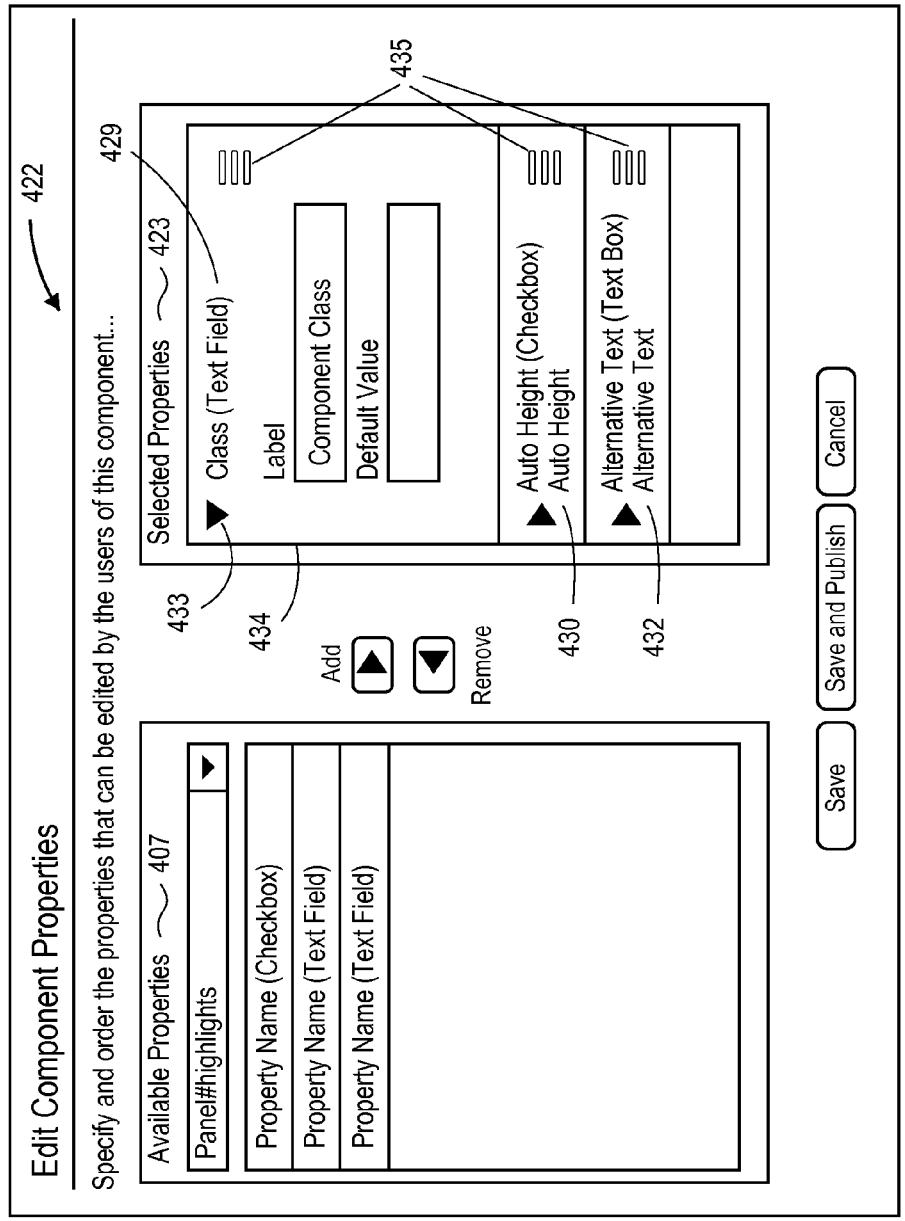
Figure 4L:
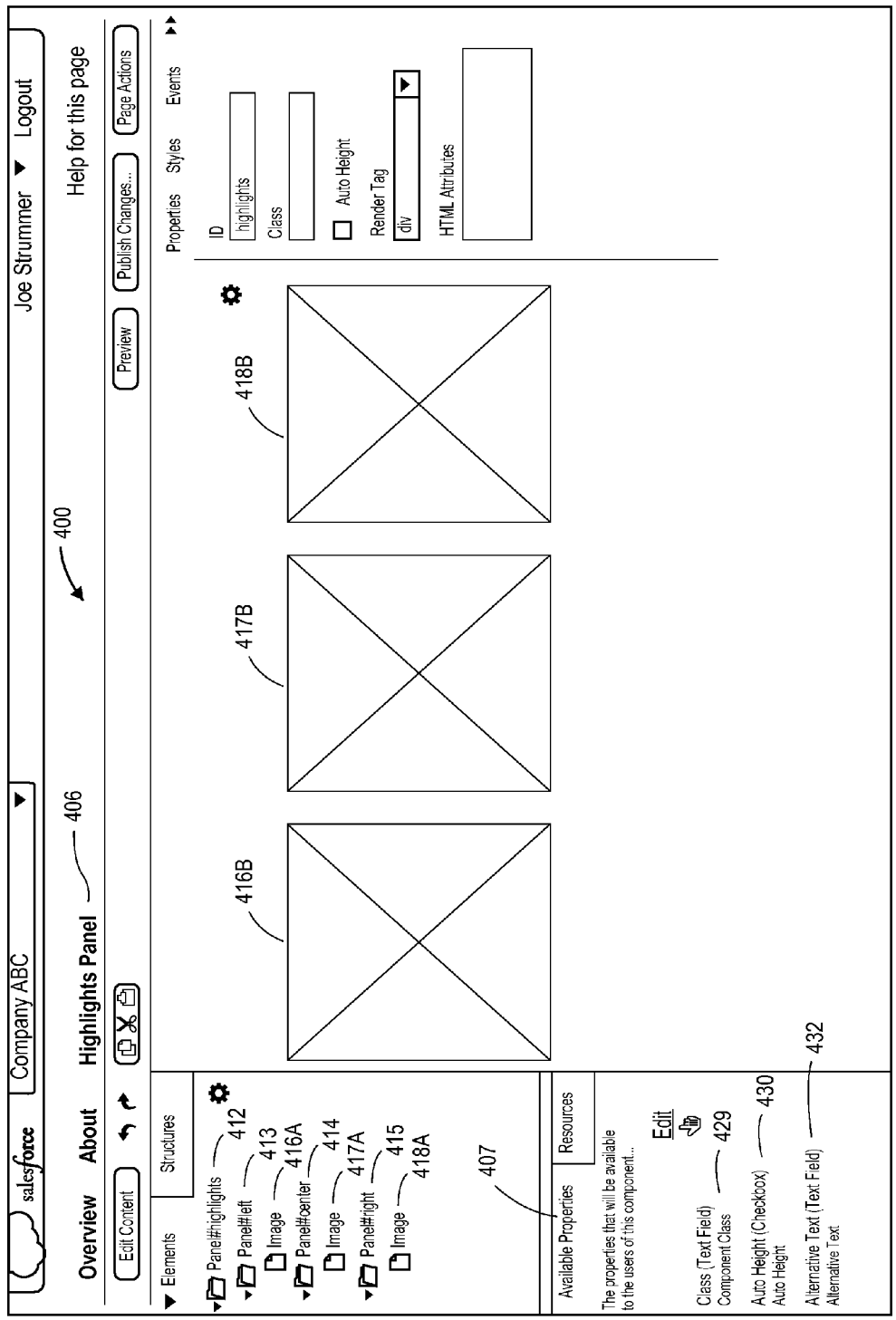

FIG. 4G illustrates a new button, such as edit 421, under available properties 407 that may be used to open a panel 422, as shown in FIG. 4H, to edit various component properties, such as moving various components from available properties 407 to selected properties 423 using a number of buttons, such as add 424, remove 425, etc., and complete or cancel the transaction by using another set of buttons, such as save 426, save and publish 427, and cancel 428. As illustrated in FIG. 4I, properties class 429 and auto heights 430 are highlighted, selected and moved to selected properties 423. Further, dropdown menu 431 may be used to select another page section of panel highlights, such as panel center 414 as shown in FIG. 4J and previously in relation to FIG. 4D. Panel 422 of FIG. 4K illustrates another property, alternative text 432, being moved from available properties 407 to selected properties 423, while class 429 is expanded into an editing panel 434 for editing certain values, such as label, default value, etc., by simply clicking on an arrow 433. Further, drag points 435 may be used to drag and reorder the selected properties 429, 430, 432. FIG. 4L illustrates a page 400 having highlights panel 406 listing available properties 407, including class 429, auto height 430, alternative text 432, and panel highlights 412, including panels 413, 414, 415, images 416A-B, 417A-B, 418A-B, and the like.

Figure 5:
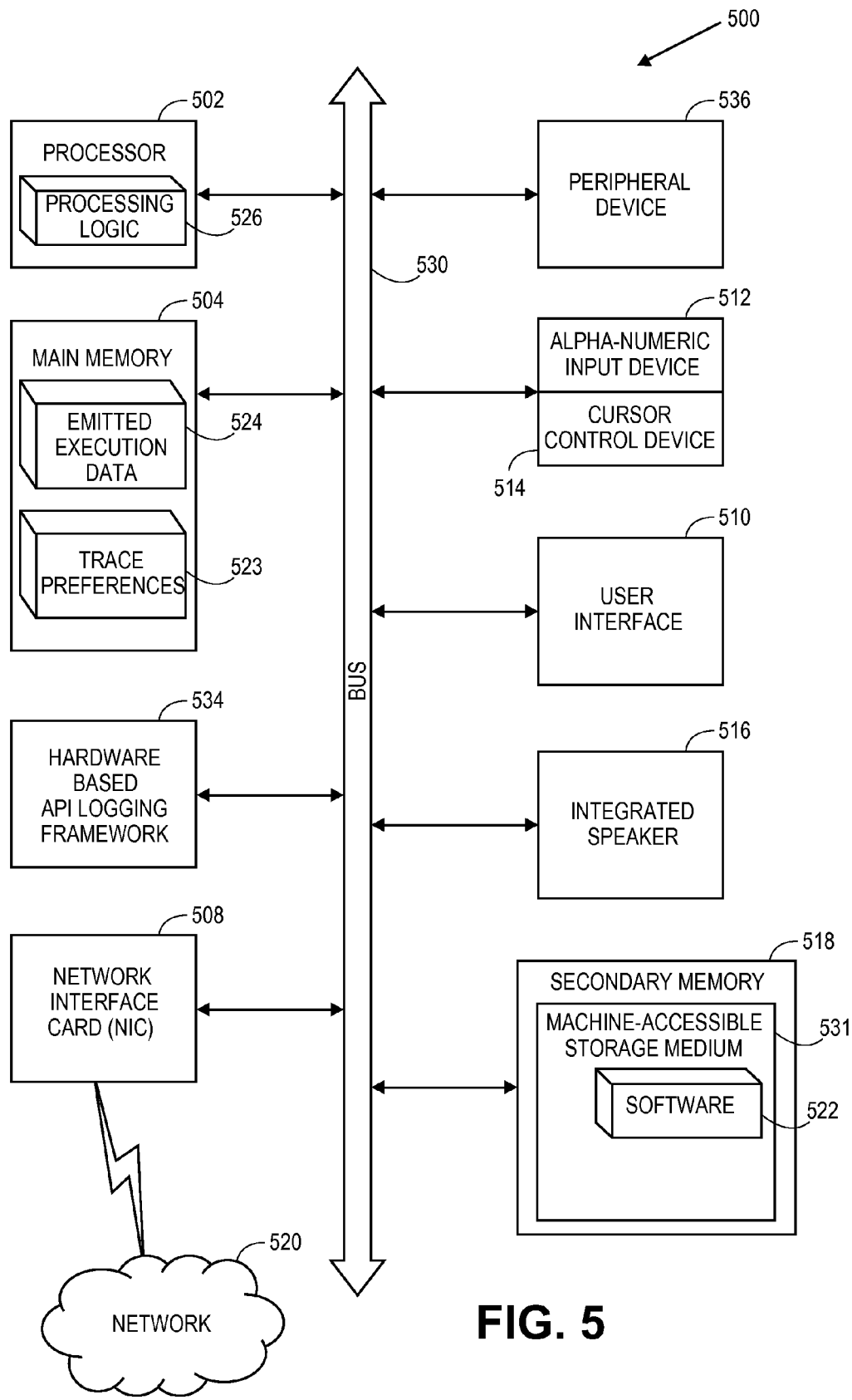
FIG. 5 illustrates a computer system according to one embodiment.

FIG. 5 illustrates a diagrammatic representation of a machine 500 in the exemplary form of a computer system, in accordance with one embodiment, within which a set of instructions, for causing the machine 500 to perform any one or more of the methodologies discussed herein, may be executed. Machine 500 is the same as or similar to computing device 100 and computing devices 230, 240 of FIG. 1 and FIG. 2, respectively. In alternative embodiments, the machine may be connected (e.g., networked) to other machines in a network (such as machine 110 of FIG. 1 connected with machines 230, 240 of FIG. 2 over network 250), such as a cloud-based network, a Local Area Network (LAN), a Wide Area Network (WAN), a Metropolitan Area Network (MAN), a Personal Area Network (PAN), an intranet, an extranet, or the Internet. The machine may operate in the capacity of a server or a client machine in a client-server network environment, or as a peer machine in a peer-to-peer (or distributed) network environment or as a server or series of servers within an on-demand service environment, including an on-demand environment providing multi-tenant database storage services. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 500 includes a processor 502, a main memory 504 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 518 (e.g., a persistent storage device including hard disk drives and persistent multi-tenant data base implementations), which communicate with each other via a bus 530. Main memory 504 includes emitted execution data 524 (e.g., data emitted by a logging framework) and one or more trace preferences 523 which operate in conjunction with processing logic 526 and processor 502 to perform the methodologies discussed herein.

Processor 502 represents one or more general-purpose processing devices such as a microprocessor, central processing unit, or the like. More particularly, the processor 502 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 502 may also be one or more special-purpose processing devices such as an application specific integrated circuit (ASIC), a field programmable gate array (FPGA), a digital signal processor (DSP), network processor, or the like. Processor 502 is configured to execute the processing logic 526 for performing the operations and functionality of dynamic customization mechanism 110 as described with reference to FIG. 1 and other figures discussed herein.

The computer system 500 may further include a network interface card 508. The computer system 500 also may include a user interface 510 (such as a video display unit, a liquid crystal display (LCD), or a cathode ray tube (CRT)), an alphanumeric input device 512 (e.g., a keyboard), a cursor control device 514 (e.g., a mouse), and a signal generation device 516 (e.g., an integrated speaker). The computer system 500 may further include peripheral device 536 (e.g., wireless or wired communication devices, memory devices, storage devices, audio processing devices, video processing devices, etc. The computer system 500 may further include a Hardware based API logging framework 534 capable of executing incoming requests for services and emitting execution data responsive to the fulfillment of such incoming requests.

The secondary memory 518 may include a machine-readable storage medium (or more specifically a machine-accessible storage medium) 531 on which is stored one or more sets of instructions (e.g., software 522) embodying any one or more of the methodologies or functions of dynamic customization mechanism 110 as described with reference to FIG. 1 and other figures described herein. The software 522 may also reside, completely or at least partially, within the main memory 504 and/or within the processor 502 during execution thereof by the computer system 500, the main memory 504 and the processor 502 also constituting machine-readable storage media. The software 522 may further be transmitted or received over a network 520 via the network interface card 508. The machine-readable storage medium 531 may include transitory or non-transitory machine-readable storage media.

Portions of various embodiments may be provided as a computer program product, which may include a computer-readable medium having stored thereon computer program instructions, which may be used to program a computer (or other electronic devices) to perform a process according to the embodiments. The machine-readable medium may include, but is not limited to, floppy diskettes, optical disks, compact disk read-only memory (CD-ROM), and magneto-optical disks, ROM, RAM, erasable programmable read-only memory (EPROM), electrically EPROM (EEPROM), magnet or optical cards, flash memory, or other type of media/machine-readable medium suitable for storing electronic instructions.

The techniques shown in the figures can be implemented using code and data stored and executed on one or more electronic devices (e.g., an end station, a network element). Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals). In addition, such electronic devices typically include a set of one or more processors coupled to one or more other components, such as one or more storage devices (non-transitory machine-readable storage media), user input/output devices (e.g., a keyboard, a touchscreen, and/or a display), and network connections. The coupling of the set of processors and other components is typically through one or more busses and bridges (also termed as bus controllers). Thus, the storage device of a given electronic device typically stores code and/or data for execution on the set of one or more processors of that electronic device. Of course, one or more parts of an embodiment may be implemented using different combinations of software, firmware, and/or hardware.

Figure 6:
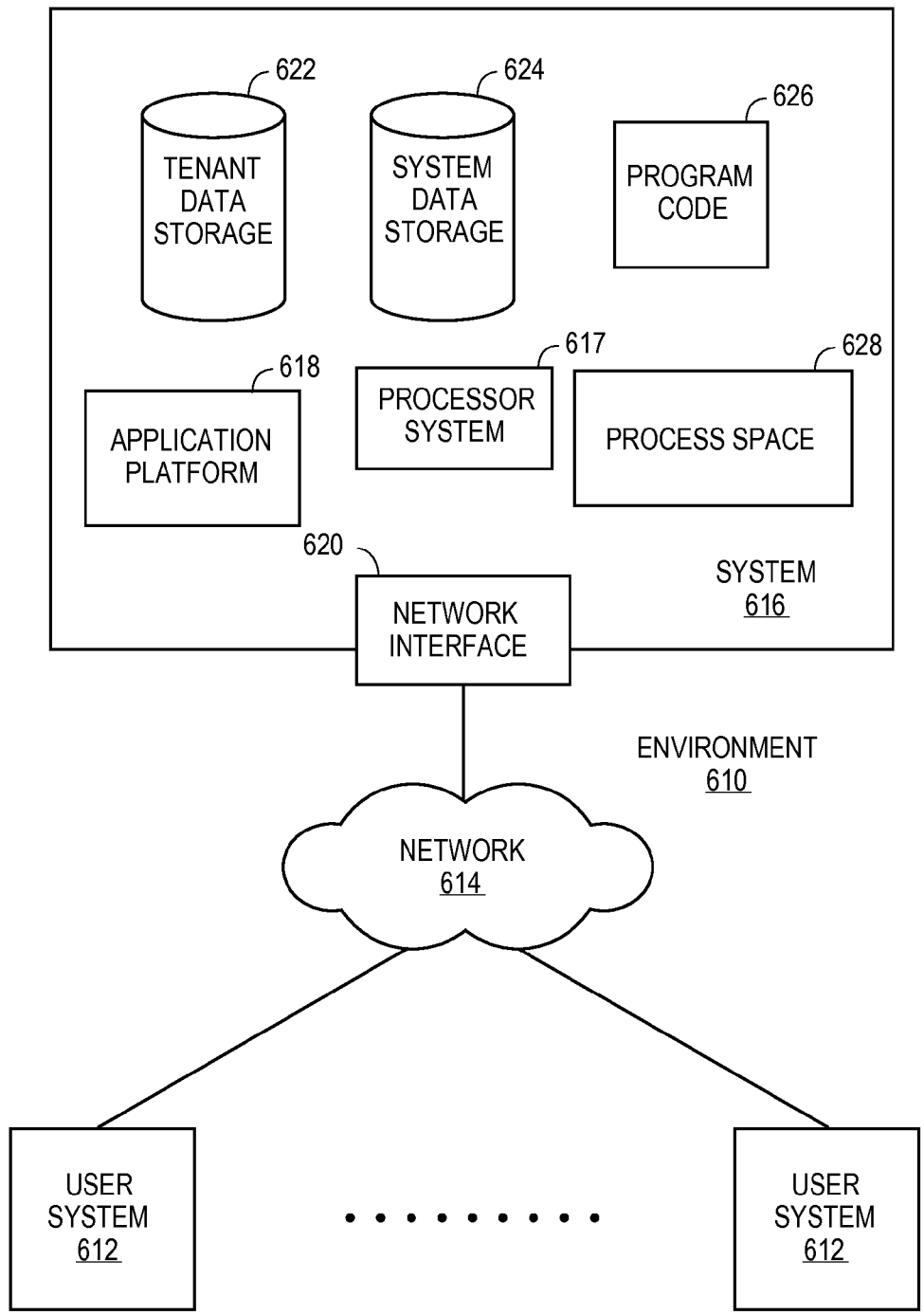
FIG. 6 illustrates a block diagram of an environment wherein an on-demand database service might be used according to one embodiment.

FIG. 6 illustrates a block diagram of an environment 610 wherein an on-demand database service might be used. Environment 610 may include user systems 612, network 614, system 616, processor system 617, application platform 618, network interface 620, tenant data storage 622, system data storage 624, program code 626, and process space 628. In other embodiments, environment 610 may not have all of the components listed and/or may have other elements instead of, or in addition to, those listed above.

Environment 610 is an environment in which an on-demand database service exists. User system 612 may be any machine or system that is used by a user to access a database user system. For example, any of user systems 612 can be a handheld computing device, a mobile phone, a laptop computer, a work station, and/or a network of computing devices. As illustrated in herein FIG. 6 (and in more detail in FIG. 7) user systems 612 might interact via a network 614 with an on-demand database service, which is system 616.

An on-demand database service, such as system 616, is a database system that is made available to outside users that do not need to necessarily be concerned with building and/or maintaining the database system, but instead may be available for their use when the users need the database system (e.g., on the demand of the users). Some on-demand database services may store information from one or more tenants stored into tables of a common database image to form a multi-tenant database system (MTS). Accordingly, "on-demand database service 616" and "system 616" will be used interchangeably herein. A database image may include one or more database objects. A relational database management system (RDMS) or the equivalent may execute storage and retrieval of information against the database object(s). Application platform 618 may be a framework that allows the applications of system 616 to run, such as the hardware and/or software, e.g., the operating system. In an embodiment, on-demand database service 616 may include an application platform 618 that enables creation, managing and executing one or more applications developed by the provider of the on-demand database service, users accessing the on-demand database service via user systems 612, or third party application developers accessing the on-demand database service via user systems 612.

The users of user systems 612 may differ in their respective capacities, and the capacity of a particular user system 612 might be entirely determined by permissions (permission levels) for the current user. For example, where a salesperson is using a particular user system 612 to interact with system 616, that user system has the capacities allotted to that salesperson. However, while an administrator is using that user system to interact with system 616, that user system has the capacities allotted to that administrator. In systems with a hierarchical role model, users at one permission level may have access to applications, data, and database information accessible by a lower permission level user, but may not have access to certain applications, database information, and data accessible by a user at a higher permission level. Thus, different users will have different capabilities with regard to accessing and modifying application and database information, depending on a user's security or permission level.

Network 614 is any network or combination of networks of devices that communicate with one another. For example, network 614 can be any one or any combination of a LAN (local area network), WAN (wide area network), telephone network, wireless network, point-to-point network, star network, token ring network, hub network, or other appropriate configuration. As the most common type of computer network in current use is a TCP/IP (Transfer Control Protocol and Internet Protocol) network, such as the global internetwork of networks often referred to as the "Internet" with a capital "I," that network will be used in many of the examples herein. However, it should be understood that the networks that one or more implementations might use are not so limited, although TCP/IP is a frequently implemented protocol.

User systems 612 might communicate with system 616 using TCP/IP and, at a higher network level, use other common Internet protocols to communicate, such as HTTP, FTP, AFS, WAP, etc. In an example where HTTP is used, user system 612 might include an HTTP client commonly referred to as a "browser" for sending and receiving HTTP messages to and from an HTTP server at system 616. Such an HTTP server might be implemented as the sole network interface between system 616 and network 614, but other techniques might be used as well or instead. In some implementations, the interface between system 616 and network 614 includes load sharing functionality, such as round-robin HTTP request distributors to balance loads and distribute incoming HTTP requests evenly over a plurality of servers. At least as for the users that are accessing that server, each of the plurality of servers has access to the MTS' data; however, other alternative configurations may be used instead.

In one embodiment, system 616, shown in FIG. 6, implements a web-based customer relationship management (CRM) system. For example, in one embodiment, system 616 includes application servers configured to implement and execute CRM software applications as well as provide related data, code, forms, webpages and other information to and from user systems 612 and to store to, and retrieve from, a database system related data, objects, and Webpage content. With a multi-tenant system, data for multiple tenants may be stored in the same physical database object, however, tenant data typically is arranged so that data of one tenant is kept logically separate from that of other tenants so that one tenant does not have access to another tenant's data, unless such data is expressly shared. In certain embodiments, system 616 implements applications other than, or in addition to, a CRM application. For example, system 616 may provide tenant access to multiple hosted (standard and custom) applications, including a CRM application. User (or third party developer) applications, which may or may not include CRM, may be supported by the application platform 618, which manages creation, storage of the applications into one or more database objects and executing of the applications in a virtual machine in the process space of the system 616.

One arrangement for elements of system 616 is shown in FIG. 6, including a network interface 620, application platform 618, tenant data storage 622 for tenant data 623, system data storage 624 for system data 625 accessible to system 616 and possibly multiple tenants, program code 626 for implementing various functions of system 616, and a process space 628 for executing MTS system processes and tenant-specific processes, such as running applications as part of an application hosting service. Additional processes that may execute on system 616 include database indexing processes.

Several elements in the system shown in FIG. 6 include conventional, well-known elements that are explained only briefly here. For example, each user system 612 could include a desktop personal computer, workstation, laptop, PDA, cell phone, or any wireless access protocol (WAP) enabled device or any other computing device capable of interfacing directly or indirectly to the Internet or other network connection. User system 612 typically runs an HTTP client, e.g., a browsing program, such as Microsoft's Internet Explorer browser, Netscape's Navigator browser, Opera's browser, or a WAP-enabled browser in the case of a cell phone, PDA or other wireless device, or the like, allowing a user (e.g., subscriber of the multi-tenant database system) of user system 612 to access, process and view information, pages and applications available to it from system 616 over network 614. Each user system 612 also typically includes one or more user interface devices, such as a keyboard, a mouse, trackball, touch pad, touch screen, pen or the like, for interacting with a graphical user interface (GUI) provided by the browser on a display (e.g., a monitor screen, LCD display, etc.) in conjunction with pages, forms, applications and other information provided by system 616 or other systems or servers. For example, the user interface device can be used to access data and applications hosted by system 616, and to perform searches on stored data, and otherwise allow a user to interact with various GUI pages that may be presented to a user. As discussed above, embodiments are suitable for use with the Internet, which refers to a specific global internetwork of networks. However, it should be understood that other networks can be used instead of the Internet, such as an intranet, an extranet, a virtual private network (VPN), a non-TCP/IP based network, any LAN or WAN or the like.

According to one embodiment, each user system 612 and all of its components are operator configurable using applications, such as a browser, including computer code run using a central processing unit such as an Intel Pentium® processor or the like. Similarly, system 616 (and additional instances of an MTS, where more than one is present) and all of their components might be operator configurable using application(s) including computer code to run using a central processing unit such as processor system 617, which may include an Intel Pentium® processor or the like, and/or multiple processor units. A computer program product embodiment includes a machine-readable storage medium (media) having instructions stored thereon/in which can be used to program a computer to perform any of the processes of the embodiments described herein. Computer code for operating and configuring system 616 to intercommunicate and to process webpages, applications and other data and media content as described herein are preferably downloaded and stored on a hard disk, but the entire program code, or portions thereof, may also be stored in any other volatile or non-volatile memory medium or device as is well known, such as a ROM or RAM, or provided on any media capable of storing program code, such as any type of rotating media including floppy disks, optical discs, digital versatile disk (DVD), compact disk (CD), microdrive, and magneto-optical disks, and magnetic or optical cards, nanosystems (including molecular memory ICs), or any type of media or device suitable for storing instructions and/or data. Additionally, the entire program code, or portions thereof, may be transmitted and downloaded from a software source over a transmission medium, e.g., over the Internet, or from another server, as is well known, or transmitted over any other conventional network connection as is well known (e.g., extranet, VPN, LAN, etc.) using any communication medium and protocols (e.g., TCP/IP, HTTP, HTTPS, Ethernet, etc.) as are well known. It will also be appreciated that computer code for implementing embodiments can be implemented in any programming language that can be executed on a client system and/or server or server system such as, for example, C, C++, HTML, any other markup language, Java™, JavaScript, ActiveX, any other scripting language, such as VBScript, and many other programming languages as are well known may be used. (Java™ is a trademark of Sun Microsystems, Inc.).

According to one embodiment, each system 616 is configured to provide webpages, forms, applications, data and media content to user (client) systems 612 to support the access by user systems 612 as tenants of system 616. As such, system 616 provides security mechanisms to keep each tenant's data separate unless the data is shared. If more than one MTS is used, they may be located in close proximity to one another (e.g., in a server farm located in a single building or campus), or they may be distributed at locations remote from one another (e.g., one or more servers located in city A and one or more servers located in city B). As used herein, each MTS could include one or more logically and/or physically connected servers distributed locally or across one or more geographic locations. Additionally, the term "server" is meant to include a computer system, including processing hardware and process space(s), and an associated storage system and database application (e.g., OODBMS or RDBMS) as is well known in the art. It should also be understood that "server system" and "server"

are often used interchangeably herein. Similarly, the database object described herein can be implemented as single databases, a distributed database, a collection of distributed databases, a database with redundant online or offline backups or other redundancies, etc., and might include a distributed database or storage network and associated processing intelligence.

Figure 7:
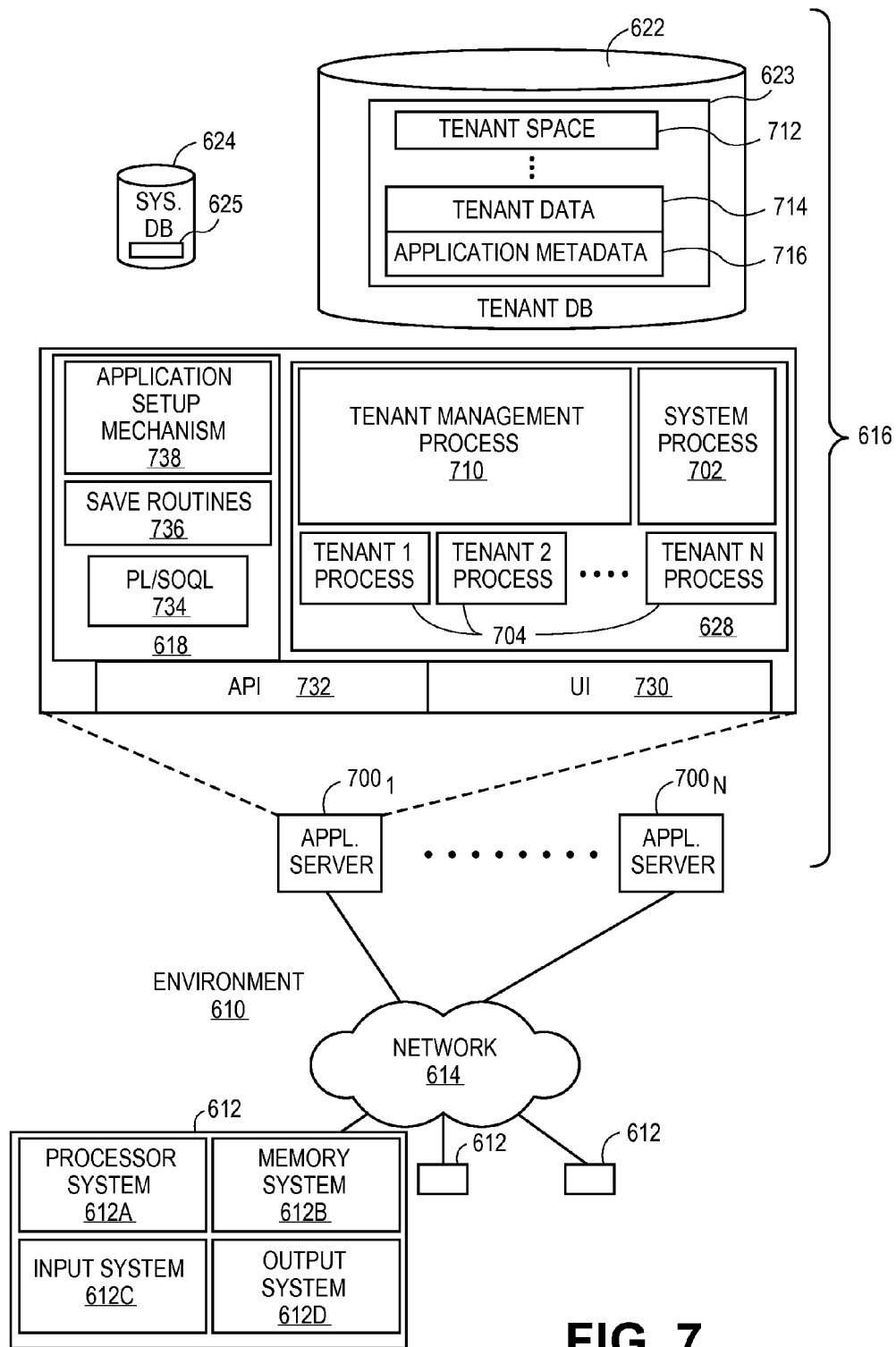
FIG. 7 illustrates a block diagram of an embodiment of elements of environment of FIG. 6 and various possible interconnections between these elements according to one embodiment.

FIG. 7 also illustrates environment 610. However, in FIG. 7 elements of system 616 and various interconnections in an embodiment are further illustrated. FIG. 7 shows that user system 612 may include processor system 612A, memory system 612B, input system 612C, and output system 612D. FIG. 7 shows network 614 and system 616. FIG. 7 also shows that system 616 may include tenant data storage 622, tenant data 623, system data storage 624, system data 625, User Interface (UI) 730, Application Program Interface (API) 732, PL/SOQL 734, save routines 736, application setup mechanism 738, applications servers $700_1$-$700_N$, system process space 702, tenant process spaces 704, tenant management process space 710, tenant storage area 712, user storage 714, and application metadata 716. In other embodiments, environment 610 may not have the same elements as those listed above and/or may have other elements instead of, or in addition to, those listed above.

User system 612, network 614, system 616, tenant data storage 622, and system data storage 624 were discussed above in FIG. 6. Regarding user system 612, processor system 612A may be any combination of one or more processors. Memory system 612B may be any combination of one or more memory devices, short term, and/or long term memory. Input system 612C may be any combination of input devices, such as one or more keyboards, mice, trackballs, scanners, cameras, and/or interfaces to networks. Output system 612D may be any combination of output devices, such as one or more monitors, printers, and/or interfaces to networks. As shown by FIG. 7, system 616 may include a network interface 620 (of FIG. 6) implemented as a set of HTTP application servers 700, an application platform 618, tenant data storage 622, and system data storage 624. Also shown is system process space 702, including individual tenant process spaces 704 and a tenant management process space 710. Each application server 700 may be configured to tenant data storage 622 and the tenant data 623 therein, and system data storage 624 and the system data 625 therein to serve requests of user systems 612. The tenant data 623 might be divided into individual tenant storage areas 712, which can be either a physical arrangement and/or a logical arrangement of data. Within each tenant storage area 712, user storage 714 and application metadata 716 might be similarly allocated for each user. For example, a copy of a user's most recently used (MRU) items might be stored to user storage 714. Similarly, a copy of MRU items for an entire organization that is a tenant might be stored to tenant storage area 712. A UI 730 provides a user interface and an API 732 provides an application programmer interface to system 616 resident processes to users and/or developers at user systems 612. The tenant data and the system data may be stored in various databases, such as one or more Oracle™ databases.

Application platform 618 includes an application setup mechanism 738 that supports application developers' creation and management of applications, which may be saved as metadata into tenant data storage 622 by save routines 736 for execution by subscribers as one or more tenant process spaces 704 managed by tenant management process 710 for example. Invocations to such applications may be coded using PL/SOQL 734 that provides a programming language style interface extension to API 732. A detailed description of some PL/SOQL language embodiments is discussed in commonly owned U.S. Pat. No. 7,730,478 entitled, "Method and System for Allowing Access to Developed Applicants via a Multi-Tenant Database On-Demand Database Service", issued Jun. 1, 2010 to Craig Weissman, which is incorporated in its entirety herein for all purposes. Invocations to applications may be detected by one or more system processes, which manage retrieving application metadata 716 for the subscriber making the invocation and executing the metadata as an application in a virtual machine.

Each application server 700 may be communicably coupled to database systems, e.g., having access to system data 625 and tenant data 623, via a different network connection. For example, one application server $700_1$ might be coupled via the network 614 (e.g., the Internet), another application server $700_{N-1}$ might be coupled via a direct network link, and another application server $700_N$ might be coupled by yet a different network connection. Transfer Control Protocol and Internet Protocol (TCP/IP) are typical protocols for communicating between application servers 700 and the database system. However, it will be apparent to one skilled in the art that other transport protocols may be used to optimize the system depending on the network interconnect used.

In certain embodiments, each application server 700 is configured to handle requests for any user associated with any organization that is a tenant. Because it is desirable to be able to add and remove application servers from the server pool at any time for any reason, there is preferably no server affinity for a user and/or organization to a specific application server 700. In one embodiment, therefore, an interface system implementing a load balancing function (e.g., an F5 Big-IP load balancer) is communicably coupled between the application servers 700 and the user systems 612 to distribute requests to the application servers 700. In one embodiment, the load balancer uses a least connections algorithm to route user requests to the application servers 700. Other examples of load balancing algorithms, such as round robin and observed response time, also can be used. For example, in certain embodiments, three consecutive requests from the same user could hit three different application servers 700, and three requests from different users could hit the same application server 700. In this manner, system 616 is multi-tenant, wherein system 616 handles storage of, and access to, different objects, data and applications across disparate users and organizations.

As an example of storage, one tenant might be a company that employs a sales force where each salesperson uses system 616 to manage their sales process. Thus, a user might maintain contact data, leads data, customer follow-up data, performance data, goals and progress data, etc., all applicable to that user's personal sales process (e.g., in tenant data storage 622). In an example of a MTS arrangement, since all of the data and the applications to access, view, modify, report, transmit, calculate, etc., can be maintained and accessed by a user system having nothing more than network access, the user can manage his or her sales efforts and cycles from any of many different user systems. For example, if a salesperson is visiting a customer and the customer has Internet access in their lobby, the salesperson can obtain critical updates as to that customer while waiting for the customer to arrive in the lobby.

While each user's data might be separate from other users' data regardless of the employers of each user, some data might be organization-wide data shared or accessible by a plurality of users or all of the users for a given organization that is a tenant. Thus, there might be some data structures managed by system 616 that are allocated at the tenant level while other data structures might be managed at the user level. Because an MTS might support multiple tenants including possible competitors, the MTS should have security protocols that keep data, applications, and application use separate. Also, because many tenants may opt for access to an MTS rather than maintain their own system, redundancy, up-time, and backup are additional functions that may be implemented in the MTS. In addition to user-specific data and tenant specific data, system 616 might also maintain system level data usable by multiple tenants or other data. Such system level data might include industry reports, news, postings, and the like that are sharable among tenants.

In certain embodiments, user systems 612 (which may be client systems) communicate with application servers 700 to request and update system-level and tenant-level data from system 616 that may require sending one or more queries to tenant data storage 622 and/or system data storage 624. System 616 (e.g., an application server 700 in system 616) automatically generates one or more SQL statements (e.g., one or more SQL queries) that are designed to access the desired information. System data storage 624 may generate query plans to access the requested data from the database.

Each database can generally be viewed as a collection of objects, such as a set of logical tables, containing data fitted into predefined categories. A "table" is one representation of a data object, and may be used herein to simplify the conceptual description of objects and custom objects. It should be understood that "table" and "object" may be used interchangeably herein. Each table generally contains one or more data categories logically arranged as columns or fields in a viewable schema. Each row or record of a table contains an instance of data for each category defined by the fields. For example, a CRM database may include a table that describes a customer with fields for basic contact information such as name, address, phone number, fax number, etc. Another table might describe a purchase order, including fields for information such as customer, product, sale price, date, etc. In some multi-tenant database systems, standard entity tables might be provided for use by all tenants. For CRM database applications, such standard entities might include tables for Account, Contact, Lead, and Opportunity data, each containing pre-defined fields. It should be understood that the word "entity" may also be used interchangeably herein with "object" and "table".

In some multi-tenant database systems, tenants may be allowed to create and store custom objects, or they may be allowed to customize standard entities or objects, for example by creating custom fields for standard objects, including custom index fields. U.S. patent application Ser. No. 10/817,161, filed Apr. 2, 2004, entitled "Custom Entities and Fields in a Multi-Tenant Database System", and which is hereby incorporated herein by reference, teaches systems and methods for creating custom objects as well as customizing standard objects in a multi-tenant database system. In certain embodiments, for example, all custom entity data rows are stored in a single multi-tenant physical table, which may contain multiple logical tables per organization. It is transparent to customers that their multiple "tables" are in fact stored in one large table or that their data may be stored in the same table as the data of other customers.

Any of the above embodiments may be used alone or together with one another in any combination. Embodiments encompassed within this specification may also include embodiments that are only partially mentioned or alluded to or are not mentioned or alluded to at all in this brief summary or in the abstract. Although various embodiments may have been motivated by various deficiencies with the prior art, which may be discussed or alluded to in one or more places in the specification, the embodiments do not necessarily address any of these deficiencies. In other words, different embodiments may address different deficiencies that may be discussed in the specification. Some embodiments may only partially address some deficiencies or just one deficiency that may be discussed in the specification, and some embodiments may not address any of these deficiencies.

While one or more implementations have been described by way of example and in terms of the specific embodiments, it is to be understood that one or more implementations are not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements. It is to be understood that the above description is intended to be illustrative, and not restrictive.

What is claimed is:

1. A computer-implemented method comprising:
   receiving, in real-time, by a server computing device, a request from a user to alter a live version of a webpage associated with the user having access to a client computing device;
   offering access, by the server computing device, to perform, via the client computing device, real-time interactive manipulation of one or more widgets associated with the webpage without employing an editable version or template of the webpage or programming code inputs relating to the one or more widgets, wherein the interactive manipulation includes at least one of interactively creating, adding, removing, defining, deploying, cross-citing, subscribing, and sharing of the one or more widgets;
   dynamically altering, in real-time, by the server computing device, the webpage based on the real-time interactive manipulation of the one or more widgets; and
   providing, in real-time, by the server computing device, the dynamically altered webpage to at least the user via the client computing device.

2. The method of claim 1, wherein the request is placed by the user, via a user interface, at the computing device, wherein the server and client computing devices are communicatively part of a network including a cloud network.

3. The method of claim 1, further comprising:
   authenticating, in real-time, the request prior to processing the request, wherein authenticating includes verifying at least one of the user, a tenant associated with the user, and the client computing device accessible to the user.

4. The method of claim 2, wherein the network further comprises one or more of a Local Area Network (LAN), a Wide Area Network (WAN), a Metropolitan Area Network (MAN), a Personal Area Network (PAN), an intranet, an extranet, and the Internet.

5. A system comprising:
   a server computing device having a memory to store instructions, and a processing device to execute the instructions to facilitate a mechanism to:
   receive, in real-time, a request from a user to alter a live version of a webpage associated with the user having access to a client computing device;

offer access to perform, via the client computing device, real-time interactive manipulation of one or more widgets associated with the webpage without employing an editable version or template of the webpage or programming code inputs relating to the one or more widgets, wherein the interactive manipulation includes at least one of interactively creating, adding, removing, defining, deploying, cross-citing, subscribing, and sharing of the one or more widgets;

dynamically alter, in real-time, the webpage based on the real-time interactive manipulation of the one or more widgets; and provide, in real-time, the dynamically altered webpage to at least the user via the client computing device.

6. The system of claim 5, wherein the request is placed by the user, via a user interface, at the computing device, wherein the server and client computing devices are communicatively part of a network including a cloud network.

7. The system of claim 5, wherein the mechanism is further to:

authenticate, in real-time, the request prior to processing the request, wherein authenticating includes verifying at least one of the user, a tenant associated with the user, and the client computing device accessible to the user.

8. The system of claim 6, wherein the network further comprises one or more of a Local Area Network (LAN), a Wide Area Network (WAN), a Metropolitan Area Network (MAN), a Personal Area Network (PAN), an intranet, an extranet, and the Internet.

9. A non-transitory machine-readable medium having stored thereon instructions which, when executed by a machine, cause the machine to:

receive, in real-time, a request from a user to alter a live version of a webpage associated with user having access to a client computing device;

offer access to perform, via the client computing device, real-time interactive manipulation of one or more widgets associated with the webpage without employing an editable version or template of the webpage or programming code inputs relating to the one or more widgets, wherein the interactive manipulation includes at least one of interactively creating, adding, removing, defining, deploying, cross-citing, subscribing, and sharing of the one or more widgets;

dynamically alter, in real-time, the webpage based on the real-time interactive manipulation of the one or more widgets; and provide, in real-time, the dynamically altered webpage to at least the user via the client computing device.

10. The non-transitory machine-readable medium of claim 9, wherein the request is placed by the user, via a user interface, at a computing device, wherein the server and client computing devices are communicatively part of network including a cloud network.

11. The non-transitory machine-readable medium of claim 9, wherein the machine is further caused to:

authenticate, in real-time, the request prior to processing the request, wherein authenticating includes verifying at least one of the user, a tenant associated with the user, and the client computing device accessible to the user.

12. The non-transitory machine-readable medium of claim 9, wherein the network further comprises one or more of a Local Area Network (LAN), a Wide Area Network (WAN), a Metropolitan Area Network (MAN), a Personal Area Network (PAN), an intranet, an extranet, and the Internet.

* * * * *